United States Patent
Zhou et al.

(10) Patent No.: US 7,919,248 B2
(45) Date of Patent: Apr. 5, 2011

(54) METHODS FOR THE MODULATION OF IL-13

(75) Inventors: Yuhong Zhou, Plymouth Meeting, PA (US); Jamila Louahed, Plymouth Meeting, PA (US); Nicholas C. Nicolaides, Plymouth Meeting, PA (US); Michael McLane, Plymouth Meeting, PA (US); Roy C. Levitt, Plymouth Meeting, PA (US)

(73) Assignee: Ligand Pharmaceuticals Incorporated, La Jolla, CA (US)

( * ) Notice: Subject to any disclaimer, the term of this patent is extended or adjusted under 35 U.S.C. 154(b) by 0 days.

(21) Appl. No.: 12/109,780

(22) Filed: Apr. 25, 2008

(65) Prior Publication Data

US 2009/0191191 A1  Jul. 30, 2009

Related U.S. Application Data

(62) Division of application No. 10/479,870, filed as application No. PCT/US02/17881 on Jun. 10, 2002, now abandoned.

(60) Provisional application No. 60/297,190, filed on Jun. 8, 2001.

(51) Int. Cl.
C12Q 1/68  (2006.01)
C12Q 1/66  (2006.01)
C12Q 1/25  (2006.01)
G01N 33/60 (2006.01)
C07H 21/02 (2006.01)

(52) U.S. Cl. .......... 435/6; 435/7.21; 435/7.9; 435/7.95; 435/8; 536/23.4; 536/23.5

(58) Field of Classification Search .................. None
See application file for complete search history.

(56) References Cited

U.S. PATENT DOCUMENTS

| | | | |
|---|---|---|---|
| 4,427,660 A | 1/1984 | Schiffman et al. | 514/18 |
| 4,703,004 A | 10/1987 | Hopp et al. | 435/69.7 |
| 4,761,375 A | 8/1988 | Clark | 435/365.1 |
| 5,116,951 A | 5/1992 | Druez et al. | 530/395 |
| 5,132,109 A | 7/1992 | Dugas et al. | 424/85.2 |
| 5,157,112 A | 10/1992 | Van Snick et al. | 530/387.9 |
| 5,164,317 A | 11/1992 | Hultner et al. | 435/386 |
| 5,180,678 A | 1/1993 | Druez et al. | 436/501 |
| 5,208,218 A | 5/1993 | Van Snick et al. | 514/8 |
| 5,246,701 A | 9/1993 | Dugas et al. | 424/158.1 |
| 5,414,071 A | 5/1995 | Yang et al. | 530/351 |
| 5,531,219 A | 7/1996 | Rosenberg | 128/203.12 |
| 5,693,762 A | 12/1997 | Queen et al. | 530/387.3 |
| 5,908,839 A | 6/1999 | Levitt et al. | 514/182 |
| 6,037,149 A | 3/2000 | Levitt et al. | 435/69.52 |
| 6,180,370 B1 | 1/2001 | Queen et al. | 39/395 |
| 6,261,559 B1 | 7/2001 | Levitt et al. | 424/139.1 |
| 6,645,492 B2 | 11/2003 | Levitt et al. | 424/139.1 |

FOREIGN PATENT DOCUMENTS

| | | |
|---|---|---|
| EP | 0361284 | 4/1990 |
| EP | 903150 | 3/1999 |
| WO | WO 90/14432 | 11/1990 |
| WO | WO 91/10738 | 7/1991 |
| WO | WO 91/14767 | 10/1991 |
| WO | WO 92/05698 | 4/1992 |
| WO | WO 97/08321 | 3/1997 |

OTHER PUBLICATIONS

Renauld et al, J Clin Pathol 54: 577-589, 2001.*
Cheng et al. (2002) Antil-Interleukin-9 Antibody Treatment Inhibits Airway Inflammation and Hyperreactivity in Mouse Asthma Model, Am. J. Respir. Crit. Med. 166:409-416.
Doull et al. (1996) Allelic association of gene markers on chromosomes 5q and 11q with atopy and bronchial hyperresponsiveness, Am. J. Respir. Crit. Care Med. 153:1280-1284.
Grunig et al. (1998) Requirement for IL-13 independently of IL-4 in experimental asthma, Science 282:2261-2263.
Huang et al. (1995) IL-13 expression at the sites of allergen challenge in patients with asthma, J. Immunol. 155:2688-2694.
Humbert et al. (1997) Elevated expression of messenger ribonucleic acid encoding IL-13 in the bronchial mucosa of atopic and nonatopic subjects with asthma, J. Allergy Clin. Immunol. 99:657-665.
Kang et al. (1995) Activation of junB and c-myc primary response genes by interleukin 9 in a human factor-dependent cell line, J Cell Physiol. 163:623-30.
Kermouni et al. ()995) The IL-9 receptor gene (IL9R): genomic structure, chromosomal localization in the pseudoautosomal region of the long arm of the sex chromosomes, and identification of IL9R pseudogenes at 9qter, 10pter, 16pter, and 18pter, Genomics. 29:371-82.
Klimka et al. (1996) A deletion mutant of Pseudomonas exotoxin-A fused to recombinant human interleukin-9 (rhIL-9-ETA') shows specific cytotoxicity against IL-9-receptor-expressing cell lines, Cytokines Mol Ther. 2:139-46.
Kung et al. (2001) Effect of Anti-mIL-9 Antibody on the Development of Pulmonary Inflammation and Airway Hyperresponsiveness in Allergic Mice, Am. J. Respir. Cell Mol. 25:600-625.
Leigh et al. (2004) Is Interleukin-13 Critical in Maintaining Airway Hyperresponsiveness in Allergen-challenged Mice, Am. J. Respir. Crit. Care Med. 851-856.
Lemoli et al. (1995) Interleukin-11 (IL-11) and IL-9 counteract the inhibitory activity of transforming growth factor beta 3 (TGF-beta 3) on human primitive hematopoietic progenitor cells, Haematologica 80:5-12.
Levitt et al. (1988) Expression of airway hyperreactivity to acetylcholine as a simple autosomal recessive trait in mice, FASEB J. 2:2605-2608.
Levitt et al. (1994) A locus regulating bronchial hyperresponsiveness maps to chromosome 5q, Amer. J. Human Genetics 55:1120.
Lopez-Valpuesta et al. (1995) Cytokines and thermoregulation: interleukin-9 injected in preoptic area fails to evoke fever in rats, Brain Res Bull. 36:181-4.

(Continued)

Primary Examiner — Phuong Huynh

(74) Attorney, Agent, or Firm — Morgan, Lewis & Bockius LLP

(57) ABSTRACT

The present invention is drawn to methods for modulating IL-13 expression and/or activity in a mammal comprising administering an effective amount of an agent which modulates the expression and/or activity of IL-9.

12 Claims, 4 Drawing Sheets

OTHER PUBLICATIONS

Marsh et al. (1994) Linkage analysis of IL4 and other chromosome 5q31.1 markers and total serum immunoglobulin E concentrations, Science 264:1152-1156.

McKenzie et al. (1993) Interleukin 13, a T-cell-derived cytokine that regulates human monocyte and B-cell function, Proc. Natl. Acad. Sci. U.S.A. 90:3735-3739.

Meyers et al. (1994) Evidence for a locus regulating total serum IgE levels mapping to chromosome 5, Genomics 23:464-470.

Minty et al. (1993) Interleukin-13 is a new human lymphokine regulating inflammatory and immune responses, Nature 362:248-250.

Mustafa et al. (2001) Elevated levels of interleukin-13 and IL-18 in patients with dengue hemorrhagic fever, FEMS Immunol. Med. Microbiol. 30:229-233.

Nassar et al. (1994) Induction of 15-lipoxygenase by interleukin-13 in human blood monocytes, J. Biol. Chem. 269:27631-27634.

Oshima et al. (2001) Interleukin-13 and interleukin-13 receptor in Hodgkin's disease possible autocrine mechanism and involvement in fibrosis, Histopathology 38:368-375.

Oriente et al. (2000) Interleukin-13 modulates collagen homeostatis in human skin and keloid fibrolasts, J. Pharmacol. Exp. Ther. 292:988-994.

Renauld et al. (1990) Expression in activated CD4+ T cells, genomic organization, and comparison with the mouse gene, J Immunol. 144:4235-4241.

Renauld et al. (1992) Expression cloning of the murine and human interleukin 9 receptor cDNAs, Proc Natl Acad Sci USA 89:5690-5694.

Renauld et al. (1995) Interleukin-9: structural characteristics and biologic properties, Cancer Treat Res. 80:287-303.

Renauld et al. (1995) Interleukin-9 and its receptor: involvement in mast cell differentiation and T cell oncogenesis, J Leukoc Biol. 57:353-60.

Renauld et al. (1996) Interleukin-9, Human Cytokines: Handbook for Basic and Clinical Research 549-559.

Rook et al. (2001) Advances in the immunopathogenesis of pulmonary tuberculosis, Curr. Opin. Pulm. Med. 7:116-123.

Rosenwasser et al. (1996) Transcriptional regulation of the human IL-9 gene in asthma and atopy, J. Investigative Medicine 44:205.

Spanbroek et al. (2001) IL-4 determines eicosanoid formation in dendritic cells by down regulation of 5-lipoxygenase and up-regulation of 15-lipoxygena 1 expression, Proc Natl Acad Sci USA 98:5152-5157.

Tenmann et al. (1998) Expression of interleukin 9 in the lungs of transgenic mice causes airway inflammation, mast cell hyperplasia, and bronchial hyperresponsiveness, J. Exp. Med. 188:1307-1320.

Townsend et al. (2000) IL-9-deficient mice establish fundamental roles for IL-9 in pulmonary mastocytosis and goblet cell hyperplasia but not T cell development, Immunity 13:573-583.

Vermeesch et al. (1995) The IL-9 receptor gene is located in the pseudoautosomal region of the long arm of the sex chromosomes, is expressed from the X and Y chromosome and its murine homologue is located on an autosome, Chromosome Research 3:105.

Walker et al. (1992) Allergic and nonallergic asthmatics have distinct patterns of T-cell activation and cytokine production in peripheral blood and bronchoalveolar lavage, Am. Rev. Respir. Dis. 146:109-115.

Wills-Karp et al. (1998) Interleukin-l3: central mediator of allergic asthma, Science, 282:2258-2261.

Yin et al. (1994) JAK1 kinase forms complexes with interleukin-4 receptor and 4PS/insulin receptor substrate-1-like protein and is activated by interleukin-4 and interleukin-9 in T lymphocytes, J Biol Chem. 269:26614-26617.

Yin et al. (1995) Interleukin-9 induces tyrosine phosphorylation of insulin receptor substrate-1 via JAK tyrosine kinases, J Biol Chem. 270:20497-502.

Yin et al. (1995) Tyrosine phosphorylation and activation of JAK family tyrosine kinases by interleukin-9 in MO7E cells, Blood 85:3101-3106.

Zhu et al. (1996) Multiple transcription factors are required for activation of human interleukin 9 gene in T cells, J Biol Chem. 271:15815-15822.

Zhu et al. Identification of critical regulatory regions in human interleukin 9 gene promoter, BLOOD, J. Amer. Soc. Hematology 86:2150 (1995).

Zhu et al. (1999) Pulmonary expression of interleukin-13 causes inflammation, mucus hypersecretion, subepithelial fibrosis, physiologic abnormalities and eotaxin production, J. Clin. Invest. 103:779-788.

* cited by examiner

SEQUENCE LISTING

<160> NUMBER OF SEQ ID NOS: 18

<210> SEQ ID NO 1
<211> LENGTH: 21
<212> TYPE: DNA
<213> ORGANISM: Mus musculus

<400> SEQUENCE: 1
tgggtgactg cagtcctggc t                                           21

<210> SEQ ID NO 2
<211> LENGTH: 21
<212> TYPE: DNA
<213> ORGANISM: Mus musculus

<400> SEQUENCE: 2
gttgctttgt gtagctgagc a                                           21

<210> SEQ ID NO 3
<211> LENGTH: 591
<212> TYPE: DNA
<213> ORGANISM: Homo sapiens
<220> FEATURE:
<221> NAME/KEY: CDS
<222> LOCATION: (12)..(446)

<400> SEQUENCE: 3
ccgctgtcaa g atg ctt ctg gcc atg gtc ctt acc tct gcc ctg ctc ctg      50
              Met Leu Leu Ala Met Val Leu Thr Ser Ala Leu Leu Leu
                1               5                  10 tgc tcc gtg gca ggc cag ggg tgt cca acc ttg gcg ggg atc ctg gac       98

```
                                                              -continued
Cys Ser Val Ala Gly Gln Gly Cys Pro Thr Leu Ala Gly Ile Leu Asp
     15                  20                  25 atc aac ttc ctc atc aac aag atg cag gaa gat cca gct tcc aag tgc    146
Ile Asn Phe Leu Ile Asn Lys Met Gln Glu Asp Pro Ala Ser Lys Cys
 30                  35                  40                  45 cac tgc agt gct aat gtg acc agt tgt ctc tgt ttg ggc att ccc tct    194
His Cys Ser Ala Asn Val Thr Ser Cys Leu Cys Leu Gly Ile Pro Ser
                 50                  55                  60 gac aac tgc acc aga cca tgc ttc agt gag aga ctg tct cag atg acc    242
Asp Asn Cys Thr Arg Pro Cys Phe Ser Glu Arg Leu Ser Gln Met Thr
             65                  70                  75 aat acc acc atg caa aca aga tac cca ctg att ttc agt cgg gtg aaa    290
Asn Thr Thr Met Gln Thr Arg Tyr Pro Leu Ile Phe Ser Arg Val Lys
         80                  85                  90 aaa tca gtt gaa gta cta aag aac aac aag tgt cca tat ttt tcc tgt    338
Lys Ser Val Glu Val Leu Lys Asn Asn Lys Cys Pro Tyr Phe Ser Cys
     95                 100                 105 gaa cag cca tgc aac caa acc acg gca ggc aac gcg ctg aca ttt ctg    386
Glu Gln Pro Cys Asn Gln Thr Thr Ala Gly Asn Ala Leu Thr Phe Leu
110                 115                 120                 125 aag agt ctt ctg gaa att ttc cag aaa gaa aag atg aga ggg atg aga    434
Lys Ser Leu Leu Glu Ile Phe Gln Lys Glu Lys Met Arg Gly Met Arg
                130                 135                 140 ggc aag ata tga agatgaaata ttatttatcc tatttattaa atttaaaaag         486
Gly Lys Ile ctttctcttt aagttgctac aatttaaaaa tcaagtaagc tactctaaat cagtatcagt    546
tgtgattatt tgtttaacat tgtatgtctt tattttgaaa taaat                   591

<210> SEQ ID NO 4
<211> LENGTH: 144
<212> TYPE: PRT
<213> ORGANISM: Homo sapiens

<400> SEQUENCE: 4

Met Leu Leu Ala Met Val Leu Thr Ser Ala Leu Leu Cys Ser Val
 1               5                  10                  15

Ala Gly Gln Gly Cys Pro Thr Leu Ala Gly Ile Leu Asp Ile Asn Phe
                 20                  25                  30

Leu Ile Asn Lys Met Gln Glu Asp Pro Ala Ser Lys Cys His Cys Ser
         35                  40                  45

Ala Asn Val Thr Ser Cys Leu Cys Leu Gly Ile Pro Ser Asp Asn Cys
     50                  55                  60

Thr Arg Pro Cys Phe Ser Glu Arg Leu Ser Gln Met Thr Asn Thr Thr
 65                  70                  75                  80

Met Gln Thr Arg Tyr Pro Leu Ile Phe Ser Arg Val Lys Lys Ser Val
                 85                  90                  95

Glu Val Leu Lys Asn Asn Lys Cys Pro Tyr Phe Ser Cys Glu Gln Pro
            100                 105                 110

Cys Asn Gln Thr Thr Ala Gly Asn Ala Leu Thr Phe Leu Lys Ser Leu
        115                 120                 125

Leu Glu Ile Phe Gln Lys Glu Lys Met Arg Gly Met Arg Gly Lys Ile
    130                 135                 140

<210> SEQ ID NO 5
<211> LENGTH: 1944
<212> TYPE: DNA
<213> ORGANISM: Homo sapiens
<220> FEATURE:
<221> NAME/KEY: CDS
```

<222> LOCATION: (180)..(1745)

<400> SEQUENCE: 5

```
agcagctctg taatgcgctt gtggtttcag atgtgggcgg cctgtgtgaa cctgtcgtgc      60
aaagctcacg tcaccaactg ctgcagttat ctcctgaatc aggctgaggg tctttgctgt     120
gcacccagag atagttgggt gacaaatcac ctccaggttg gggatgcctc agacttgtg     179
```

| | | | | | | | | | | | | | | | | |
|---|---|---|---|---|---|---|---|---|---|---|---|---|---|---|---|---|
| atg | gga | ctg | ggc | aga | tgc | atc | tgg | gaa | ggc | tgg | acc | ttg | gag | agt | gag | 227 |
| Met | Gly | Leu | Gly | Arg | Cys | Ile | Trp | Glu | Gly | Trp | Thr | Leu | Glu | Ser | Glu | |
| 1 | | | | 5 | | | | | 10 | | | | | 15 | | |

| gcc | ctg | agg | cga | gac | atg | ggc | acc | tgg | ctc | ctg | gcc | tgc | atc | tgc | atc | 275 |
|---|---|---|---|---|---|---|---|---|---|---|---|---|---|---|---|---|
| Ala | Leu | Arg | Arg | Asp | Met | Gly | Thr | Trp | Leu | Leu | Ala | Cys | Ile | Cys | Ile | |
| | | | 20 | | | | | 25 | | | | | 30 | | | |

| tgc | acc | tgt | gtc | tgc | ttg | gga | gtc | tct | gtc | aca | ggg | gaa | gga | caa | ggg | 323 |
|---|---|---|---|---|---|---|---|---|---|---|---|---|---|---|---|---|
| Cys | Thr | Cys | Val | Cys | Leu | Gly | Val | Ser | Val | Thr | Gly | Glu | Gly | Gln | Gly | |
| | | 35 | | | | | 40 | | | | | 45 | | | | |

| cca | agg | tct | aga | acc | ttc | acc | tgc | ctc | acc | aac | aac | att | ctc | agg | atc | 371 |
|---|---|---|---|---|---|---|---|---|---|---|---|---|---|---|---|---|
| Pro | Arg | Ser | Arg | Thr | Phe | Thr | Cys | Leu | Thr | Asn | Asn | Ile | Leu | Arg | Ile | |
| 50 | | | | | 55 | | | | | 60 | | | | | | |

| gat | tgc | cac | tgg | tct | gcc | cca | gag | ctg | gga | cag | ggc | tcc | agc | ccc | tgg | 419 |
|---|---|---|---|---|---|---|---|---|---|---|---|---|---|---|---|---|
| Asp | Cys | His | Trp | Ser | Ala | Pro | Glu | Leu | Gly | Gln | Gly | Ser | Ser | Pro | Trp | |
| 65 | | | | 70 | | | | | 75 | | | | | 80 | | |

| ctc | ctc | ttc | acc | agc | aac | cag | gct | cct | ggc | ggc | aca | cat | aag | tgc | atc | 467 |
|---|---|---|---|---|---|---|---|---|---|---|---|---|---|---|---|---|
| Leu | Leu | Phe | Thr | Ser | Asn | Gln | Ala | Pro | Gly | Gly | Thr | His | Lys | Cys | Ile | |
| | | | | 85 | | | | | 90 | | | | | 95 | | |

| ttg | cgg | ggc | agt | gag | tgc | acc | gtc | gtg | ctg | cca | cct | gag | gca | gtg | ctc | 515 |
|---|---|---|---|---|---|---|---|---|---|---|---|---|---|---|---|---|
| Leu | Arg | Gly | Ser | Glu | Cys | Thr | Val | Val | Leu | Pro | Pro | Glu | Ala | Val | Leu | |
| | | | 100 | | | | | 105 | | | | | 110 | | | |

| gtg | cca | tct | gac | aat | ttc | acc | atc | act | ttc | cac | cac | tgc | atg | tct | ggg | 563 |
|---|---|---|---|---|---|---|---|---|---|---|---|---|---|---|---|---|
| Val | Pro | Ser | Asp | Asn | Phe | Thr | Ile | Thr | Phe | His | His | Cys | Met | Ser | Gly | |
| | | 115 | | | | | 120 | | | | | 125 | | | | |

| agg | gag | cag | gtc | agc | ctg | gtg | gac | ccg | gag | tac | ctg | ccc | cgg | aga | cac | 611 |
|---|---|---|---|---|---|---|---|---|---|---|---|---|---|---|---|---|
| Arg | Glu | Gln | Val | Ser | Leu | Val | Asp | Pro | Glu | Tyr | Leu | Pro | Arg | Arg | His | |
| 130 | | | | | 135 | | | | | 140 | | | | | | |

| gtt | aag | ctg | gac | ccg | ccc | tct | gac | ttg | cag | agc | aac | atc | agt | tct | ggc | 659 |
|---|---|---|---|---|---|---|---|---|---|---|---|---|---|---|---|---|
| Val | Lys | Leu | Asp | Pro | Pro | Ser | Asp | Leu | Gln | Ser | Asn | Ile | Ser | Ser | Gly | |
| 145 | | | | 150 | | | | | 155 | | | | | 160 | | |

| cac | tgc | atc | ctg | acc | tgg | agc | atc | agt | cct | gcc | ttg | gag | cca | atg | acc | 707 |
|---|---|---|---|---|---|---|---|---|---|---|---|---|---|---|---|---|
| His | Cys | Ile | Leu | Thr | Trp | Ser | Ile | Ser | Pro | Ala | Leu | Glu | Pro | Met | Thr | |
| | | | 165 | | | | | 170 | | | | | 175 | | | |

| aca | ctt | ctc | agc | tat | gag | ctg | gcc | ttc | aag | aag | cag | gaa | gag | gcc | tgg | 755 |
|---|---|---|---|---|---|---|---|---|---|---|---|---|---|---|---|---|
| Thr | Leu | Leu | Ser | Tyr | Glu | Leu | Ala | Phe | Lys | Lys | Gln | Glu | Glu | Ala | Trp | |
| | | | 180 | | | | | 185 | | | | | 190 | | | |

| gag | cag | gcc | cag | cac | agg | gat | cac | att | gtc | ggg | gtg | acc | tgg | ctt | ata | 803 |
|---|---|---|---|---|---|---|---|---|---|---|---|---|---|---|---|---|
| Glu | Gln | Ala | Gln | His | Arg | Asp | His | Ile | Val | Gly | Val | Thr | Trp | Leu | Ile | |
| | | | 195 | | | | | 200 | | | | | 205 | | | |

| ctt | gaa | gcc | ttt | gag | ctg | gac | cct | ggc | ttt | atc | cat | gag | gcc | agg | ctg | 851 |
|---|---|---|---|---|---|---|---|---|---|---|---|---|---|---|---|---|
| Leu | Glu | Ala | Phe | Glu | Leu | Asp | Pro | Gly | Phe | Ile | His | Glu | Ala | Arg | Leu | |
| | 210 | | | | | 215 | | | | | 220 | | | | | |

| cgt | gtc | cag | atg | gcc | aca | ctg | gag | gat | gat | gtg | gta | gag | gag | gag | cgt | 899 |
|---|---|---|---|---|---|---|---|---|---|---|---|---|---|---|---|---|
| Arg | Val | Gln | Met | Ala | Thr | Leu | Glu | Asp | Asp | Val | Val | Glu | Glu | Glu | Arg | |
| 225 | | | | | 230 | | | | | 235 | | | | | 240 | |

| tat | aca | ggc | cag | tgg | agt | gag | tgg | agc | cag | cct | gtg | tgc | ttc | cag | gct | 947 |
|---|---|---|---|---|---|---|---|---|---|---|---|---|---|---|---|---|
| Tyr | Thr | Gly | Gln | Trp | Ser | Glu | Trp | Ser | Gln | Pro | Val | Cys | Phe | Gln | Ala | |
| | | | | 245 | | | | | 250 | | | | | 255 | | |

| ccc | cag | aga | caa | ggc | cct | ctg | atc | cca | ccc | tgg | ggg | tgg | cca | ggc | aac | 995 |
|---|---|---|---|---|---|---|---|---|---|---|---|---|---|---|---|---|
| Pro | Gln | Arg | Gln | Gly | Pro | Leu | Ile | Pro | Pro | Trp | Gly | Trp | Pro | Gly | Asn | |
| | | | 260 | | | | | 265 | | | | | 270 | | | |

| acc | ctt | gtt | gct | gtg | tcc | atc | ttt | ctc | ctg | ctg | act | ggc | ccg | acc | tac | 1043 |
|---|---|---|---|---|---|---|---|---|---|---|---|---|---|---|---|---|
| Thr | Leu | Val | Ala | Val | Ser | Ile | Phe | Leu | Leu | Leu | Thr | Gly | Pro | Thr | Tyr | |

```
                        275                 280                 285
ctc ctg ttc aag ctg tcg ccc agg gtg aag aga atc ttc tac cag aac    1091
Leu Leu Phe Lys Leu Ser Pro Arg Val Lys Arg Ile Phe Tyr Gln Asn
    290                 295                 300 gtg ccc tct cca gcg atg ttc ttc cag ccc ctc tac agt gta cac aat    1139
Val Pro Ser Pro Ala Met Phe Phe Gln Pro Leu Tyr Ser Val His Asn
305                 310                 315                 320 ggg aac ttc cag act tgg atg ggg gcc cac ggg gcc ggt gtg ctg ttg    1187
Gly Asn Phe Gln Thr Trp Met Gly Ala His Gly Ala Gly Val Leu Leu
            325                 330                 335 agc cag gac tgt gct ggc acc cca cag gga gcc ttg gag ccc tgc gtc    1235
Ser Gln Asp Cys Ala Gly Thr Pro Gln Gly Ala Leu Glu Pro Cys Val
        340                 345                 350 cag gag gcc act gca ctg ctc act tgt ggc cca gcg cgt cct tgg aaa    1283
Gln Glu Ala Thr Ala Leu Leu Thr Cys Gly Pro Ala Arg Pro Trp Lys
    355                 360                 365 tct gtg gcc ctg gag gag gaa cag gag ggc cct ggg acc agg ctc ccg    1331
Ser Val Ala Leu Glu Glu Glu Gln Glu Gly Pro Gly Thr Arg Leu Pro
370                 375                 380 ggg aac ctg agc tca gag gat gtg ctg cca gca ggg tgt acg gag tgg    1379
Gly Asn Leu Ser Ser Glu Asp Val Leu Pro Ala Gly Cys Thr Glu Trp
385                 390                 395                 400 agg gta cag acg ctt gcc tat ctg cca cag gag gac tgg gcc ccc acg    1427
Arg Val Gln Thr Leu Ala Tyr Leu Pro Gln Glu Asp Trp Ala Pro Thr
            405                 410                 415 tcc ctg act agg ccg gct ccc cca gac tca gag ggc agc agg agc agc    1475
Ser Leu Thr Arg Pro Ala Pro Pro Asp Ser Glu Gly Ser Arg Ser Ser
        420                 425                 430 agc agc agc agc agc aac aac aac aac tac tgt gcc ttg ggc tgc        1523
Ser Ser Ser Ser Ser Asn Asn Asn Asn Tyr Cys Ala Leu Gly Cys
    435                 440                 445 tat ggg gga tgg cac ctc tca gcc ctc cca gga aac aca cag agc tct    1571
Tyr Gly Gly Trp His Leu Ser Ala Leu Pro Gly Asn Thr Gln Ser Ser
450                 455                 460 ggg ccc atc cca gcc ctg gcc tgt ggc ctt tct tgt gac cat cag ggc    1619
Gly Pro Ile Pro Ala Leu Ala Cys Gly Leu Ser Cys Asp His Gln Gly
465                 470                 475                 480 ctg gag acc cag caa gga gtt gcc tgg gtg ctg gct ggt cac tgc cag    1667
Leu Glu Thr Gln Gln Gly Val Ala Trp Val Leu Ala Gly His Cys Gln
            485                 490                 495 agg cct ggg ctg cat gag gac ctc cag ggc atg ttg ctc cct tct gtc    1715
Arg Pro Gly Leu His Glu Asp Leu Gln Gly Met Leu Leu Pro Ser Val
        500                 505                 510 ctc agc aag gct cgg tcc tgg aca ttc tag gtccctgact cgccagatgc     1765
Leu Ser Lys Ala Arg Ser Trp Thr Phe
    515                 520 atcatgtcca ttttgggaaa atggactgaa gtttctggag cccttgtctg agactgaacc  1825
tcctgagaag gggcccctag cagcggtcag aggtcctgtc tggatggagg ctggaggctc  1885 cccccctcaac ccctctgctc agtgcctgtg gggagcagcc tctaccctca gcatcctgg   1944

<210> SEQ ID NO 6
<211> LENGTH: 521
<212> TYPE: PRT
<213> ORGANISM: Homo sapiens

<400> SEQUENCE: 6

Met Gly Leu Gly Arg Cys Ile Trp Glu Gly Trp Thr Leu Glu Ser Glu
1               5                   10                  15

Ala Leu Arg Arg Asp Met Gly Thr Trp Leu Leu Ala Cys Ile Cys Ile
```

```
                20                  25                  30
Cys Thr Cys Val Cys Leu Gly Val Ser Val Thr Gly Glu Gly Gln Gly
             35                  40                  45

Pro Arg Ser Arg Thr Phe Thr Cys Leu Thr Asn Asn Ile Leu Arg Ile
 50                  55                  60

Asp Cys His Trp Ser Ala Pro Glu Leu Gly Gln Gly Ser Ser Pro Trp
 65                  70                  75                  80

Leu Leu Phe Thr Ser Asn Gln Ala Pro Gly Thr His Lys Cys Ile
             85                  90                  95

Leu Arg Gly Ser Glu Cys Thr Val Val Leu Pro Pro Glu Ala Val Leu
            100                 105                 110

Val Pro Ser Asp Asn Phe Thr Ile Thr Phe His His Cys Met Ser Gly
            115                 120                 125

Arg Glu Gln Val Ser Leu Val Asp Pro Glu Tyr Leu Pro Arg Arg His
            130                 135                 140

Val Lys Leu Asp Pro Pro Ser Asp Leu Gln Ser Asn Ile Ser Ser Gly
145                 150                 155                 160

His Cys Ile Leu Thr Trp Ser Ile Ser Pro Ala Leu Glu Pro Met Thr
                165                 170                 175

Thr Leu Leu Ser Tyr Glu Leu Ala Phe Lys Lys Gln Glu Glu Ala Trp
                180                 185                 190

Glu Gln Ala Gln His Arg Asp His Ile Val Gly Val Thr Trp Leu Ile
            195                 200                 205

Leu Glu Ala Phe Glu Leu Asp Pro Gly Phe Ile His Glu Ala Arg Leu
            210                 215                 220

Arg Val Gln Met Ala Thr Leu Glu Asp Asp Val Val Glu Glu Glu Arg
225                 230                 235                 240

Tyr Thr Gly Gln Trp Ser Glu Trp Ser Gln Pro Val Cys Phe Gln Ala
                245                 250                 255

Pro Gln Arg Gln Gly Pro Leu Ile Pro Pro Trp Gly Trp Pro Gly Asn
            260                 265                 270

Thr Leu Val Ala Val Ser Ile Phe Leu Leu Leu Thr Gly Pro Thr Tyr
            275                 280                 285

Leu Leu Phe Lys Leu Ser Pro Arg Val Lys Arg Ile Phe Tyr Gln Asn
290                 295                 300

Val Pro Ser Pro Ala Met Phe Phe Gln Pro Leu Tyr Ser Val His Asn
305                 310                 315                 320

Gly Asn Phe Gln Thr Trp Met Gly Ala His Gly Ala Gly Val Leu Leu
                325                 330                 335

Ser Gln Asp Cys Ala Gly Thr Pro Gln Gly Ala Leu Glu Pro Cys Val
            340                 345                 350

Gln Glu Ala Thr Ala Leu Leu Thr Cys Gly Pro Ala Arg Pro Trp Lys
            355                 360                 365

Ser Val Ala Leu Glu Glu Glu Glu Gly Pro Gly Thr Arg Leu Pro
            370                 375                 380

Gly Asn Leu Ser Ser Glu Asp Val Leu Pro Ala Gly Cys Thr Glu Trp
385                 390                 395                 400

Arg Val Gln Thr Leu Ala Tyr Leu Pro Gln Glu Asp Trp Ala Pro Thr
                405                 410                 415

Ser Leu Thr Arg Pro Ala Pro Pro Asp Ser Glu Gly Ser Arg Ser Ser
                420                 425                 430

Ser Ser Ser Ser Ser Asn Asn Asn Asn Tyr Cys Ala Leu Gly Cys
            435                 440                 445
```

```
Tyr Gly Gly Trp His Leu Ser Ala Leu Pro Gly Asn Thr Gln Ser Ser
        450                 455                 460

Gly Pro Ile Pro Ala Leu Ala Cys Gly Leu Ser Cys Asp His Gln Gly
465                 470                 475                 480

Leu Glu Thr Gln Gln Gly Val Ala Trp Val Leu Ala Gly His Cys Gln
                    485                 490                 495

Arg Pro Gly Leu His Glu Asp Leu Gln Gly Met Leu Leu Pro Ser Val
            500                 505                 510

Leu Ser Lys Ala Arg Ser Trp Thr Phe
        515                 520

<210> SEQ ID NO 7
<211> LENGTH: 536
<212> TYPE: DNA
<213> ORGANISM: Mus musculus
<220> FEATURE:
<221> NAME/KEY: CDS
<222> LOCATION: (16)..(450)

<400> SEQUENCE: 7
cagactcccg tcaac atg ttg gtg aca tac atc ctt gcc tct gtt ttg ctc         51
              Met Leu Val Thr Tyr Ile Leu Ala Ser Val Leu Leu
                1               5                   10 ttc agt tct gtg ctg ggc cag aga tgc agc acc aca tgg ggc atc aga         99
Phe Ser Ser Val Leu Gly Gln Arg Cys Ser Thr Thr Trp Gly Ile Arg
            15                  20                  25 gac acc aat tac ctt att gaa aat ctg aag gat gat cca ccg tca aaa        147
Asp Thr Asn Tyr Leu Ile Glu Asn Leu Lys Asp Asp Pro Pro Ser Lys
 30                  35                  40 tgc agc tgc agc ggc aac gtg acc agc tgc ttg tgt ctc tcc gtc cca        195
Cys Ser Cys Ser Gly Asn Val Thr Ser Cys Leu Cys Leu Ser Val Pro
 45                  50                  55                  60 act gat gat tgt acc aca ccg tgc tac agg gag gga ctg tta cag ctg        243
Thr Asp Asp Cys Thr Thr Pro Cys Tyr Arg Glu Gly Leu Leu Gln Leu
                     65                  70                  75 acc aat gcc aca cag aaa tca aga ctc ttg cct gtt ttc cat cgg gtg        291
Thr Asn Ala Thr Gln Lys Ser Arg Leu Leu Pro Val Phe His Arg Val
         80                  85                  90 aaa agg ata gtt gaa gtc cta aag aac atc acg tgt ccg tcc ttt tcc        339
Lys Arg Ile Val Glu Val Leu Lys Asn Ile Thr Cys Pro Ser Phe Ser
     95                  100                 105 tgc gaa aag cca tgc aac cag acc atg gca ggc aac aca ctg tca ttt        387
Cys Glu Lys Pro Cys Asn Gln Thr Met Ala Gly Asn Thr Leu Ser Phe
110                 115                 120 ctg aag agt ctc ctg ggg acg ttc cag aag aca gag atg caa agg cag        435
Leu Lys Ser Leu Leu Gly Thr Phe Gln Lys Thr Glu Met Gln Arg Gln
125                 130                 135                 140 aaa agc cga cca tga agacagatgc tatttattct atttattgaa tttacaaaac        490
Lys Ser Arg Pro ctcccctcct taactgttac agtgaagaaa taaactaagc tattct                     536

<210> SEQ ID NO 8
<211> LENGTH: 144
<212> TYPE: PRT
<213> ORGANISM: Mus musculus

<400> SEQUENCE: 8

Met Leu Val Thr Tyr Ile Leu Ala Ser Val Leu Leu Phe Ser Ser Val
  1               5                   10                  15

Leu Gly Gln Arg Cys Ser Thr Thr Trp Gly Ile Arg Asp Thr Asn Tyr
             20                  25                  30
```

```
Leu Ile Glu Asn Leu Lys Asp Asp Pro Pro Ser Lys Cys Ser Cys Ser
            35                  40                  45

Gly Asn Val Thr Ser Cys Leu Cys Leu Ser Val Pro Thr Asp Asp Cys
 50                  55                  60

Thr Thr Pro Cys Tyr Arg Glu Gly Leu Leu Gln Leu Thr Asn Ala Thr
 65                  70                  75                  80

Gln Lys Ser Arg Leu Leu Pro Val Phe His Arg Val Lys Arg Ile Val
            85                  90                  95

Glu Val Leu Lys Asn Ile Thr Cys Pro Ser Phe Ser Cys Glu Lys Pro
            100                 105                 110

Cys Asn Gln Thr Met Ala Gly Asn Thr Leu Ser Phe Leu Lys Ser Leu
            115                 120                 125

Leu Gly Thr Phe Gln Lys Thr Glu Met Gln Arg Gln Lys Ser Arg Pro
            130                 135                 140
```

```
<210> SEQ ID NO 9
<211> LENGTH: 3026
<212> TYPE: DNA
<213> ORGANISM: Mus musculus
<220> FEATURE:
<221> NAME/KEY: CDS
<222> LOCATION: (5)..(1411)

<400> SEQUENCE: 9
```

```
ctcc atg gcc ctg gga aga tgc att gcg gaa ggt tgg acc ttg gag aga          49
     Met Ala Leu Gly Arg Cys Ile Ala Glu Gly Trp Thr Leu Glu Arg
      1               5                  10                  15 gtg gcg gtg aaa cag gtc tcc tgg ttc ctg atc tac agc tgg gtc tgc          97
Val Ala Val Lys Gln Val Ser Trp Phe Leu Ile Tyr Ser Trp Val Cys
                 20                  25                  30 tct gga gtc tgc cgg gga gtc tcg gtc cca gag caa gga gga gga ggg         145
Ser Gly Val Cys Arg Gly Val Ser Val Pro Glu Gln Gly Gly Gly Gly
             35                  40                  45 cag aag gct gga gca ttc acc tgt ctc agc aac agt att tac agg atc         193
Gln Lys Ala Gly Ala Phe Thr Cys Leu Ser Asn Ser Ile Tyr Arg Ile
         50                  55                  60 gac tgc cac tgg tcg gct cca gag ctg ggc cag gaa tcc agg gcc tgg         241
Asp Cys His Trp Ser Ala Pro Glu Leu Gly Gln Glu Ser Arg Ala Trp
 65                  70                  75 ctc ctc ttt acc agt aac cag gtg act gaa atc aaa cac aaa tgc acc         289
Leu Leu Phe Thr Ser Asn Gln Val Thr Glu Ile Lys His Lys Cys Thr
 80                  85                  90                  95 ttc tgg gac agt atg tgt acc ctg gtg ctg cct aaa gag gag gtg ttc         337
Phe Trp Asp Ser Met Cys Thr Leu Val Leu Pro Lys Glu Glu Val Phe
                 100                 105                 110 tta cct ttt gac aac ttc acc atc aca ctt cac cgc tgc atc atg gga         385
Leu Pro Phe Asp Asn Phe Thr Ile Thr Leu His Arg Cys Ile Met Gly
             115                 120                 125 cag gaa cag gtc agc ctg gtg gac tca cag tac ctg ccc agg aga cac         433
Gln Glu Gln Val Ser Leu Val Asp Ser Gln Tyr Leu Pro Arg Arg His
         130                 135                 140 atc aag ttg gac cca ccc tct gat ctg cag agc aat gtc agc tct ggg         481
Ile Lys Leu Asp Pro Pro Ser Asp Leu Gln Ser Asn Val Ser Ser Gly
145                 150                 155 cgt tgt gtc ctg acc tgg ggt atc aat ctt gcc ctg gag cca ttg atc         529
Arg Cys Val Leu Thr Trp Gly Ile Asn Leu Ala Leu Glu Pro Leu Ile
160                 165                 170                 175 aca tcc ctc agc tac gag ctg gcc ttc aag agg cag gaa gag gcc tgg         577
Thr Ser Leu Ser Tyr Glu Leu Ala Phe Lys Arg Gln Glu Glu Ala Trp
                 180                 185                 190
```

```
gag gcc cgg cac aag gac cgt atc gtt gga gtg acc tgg ctc atc ctt        625
Glu Ala Arg His Lys Asp Arg Ile Val Gly Val Thr Trp Leu Ile Leu
            195                 200                 205 gaa gcc gtc gaa ctg aat cct ggt tcc atc tac gag gcc agg ctg cgt        673
Glu Ala Val Glu Leu Asn Pro Gly Ser Ile Tyr Glu Ala Arg Leu Arg
        210                 215                 220 gtc cag atg act ttg gag agt tat gag gac aag aca gag ggg gaa tat        721
Val Gln Met Thr Leu Glu Ser Tyr Glu Asp Lys Thr Glu Gly Glu Tyr
    225                 230                 235 tat aag agc cat tgg agt gag tgg agc cag ccc gtg tcc ttt cct tct        769
Tyr Lys Ser His Trp Ser Glu Trp Ser Gln Pro Val Ser Phe Pro Ser
240                 245                 250                 255 ccc cag agg aga cag ggc ctc ctg gtc cca cgc tgg caa tgg tca gcc        817
Pro Gln Arg Arg Gln Gly Leu Leu Val Pro Arg Trp Gln Trp Ser Ala
                260                 265                 270 agc atc ctt gta gtt gtg ccc atc ttt ctt ctg act ggc ttt gtc            865
Ser Ile Leu Val Val Val Pro Ile Phe Leu Leu Thr Gly Phe Val
            275                 280                 285 cac ctt ctg ttc aag ctg tca ccc agg ctg aag aga atc ttt tac cag        913
His Leu Leu Phe Lys Leu Ser Pro Arg Leu Lys Arg Ile Phe Tyr Gln
        290                 295                 300 aac att cca tct ccc gag gcg ttc ttc cat cct ctc tac agt gtg tac        961
Asn Ile Pro Ser Pro Glu Ala Phe Phe His Pro Leu Tyr Ser Val Tyr
    305                 310                 315 cat ggg gac ttc cag agt tgg aca ggg gcc cgc aga gcc gga cca caa       1009
His Gly Asp Phe Gln Ser Trp Thr Gly Ala Arg Arg Ala Gly Pro Gln
320                 325                 330                 335 gca aga cag aat ggt gtc agt act tca tca gca ggc tca gag tcc agc       1057
Ala Arg Gln Asn Gly Val Ser Thr Ser Ser Ala Gly Ser Glu Ser Ser
                340                 345                 350 atc tgg gag gcc gtc gcc aca ctc acc tat agc ccg gca tgc cct gtg       1105
Ile Trp Glu Ala Val Ala Thr Leu Thr Tyr Ser Pro Ala Cys Pro Val
            355                 360                 365 cag ttt gcc tgc ctg aag tgg gag gcc aca gcc ccg ggc ttc cca ggg       1153
Gln Phe Ala Cys Leu Lys Trp Glu Ala Thr Ala Pro Gly Phe Pro Gly
        370                 375                 380 ctc cca ggc tca gag cat gtg ctg ccg gca ggg tgt ctg gag ttg gaa       1201
Leu Pro Gly Ser Glu His Val Leu Pro Ala Gly Cys Leu Glu Leu Glu
    385                 390                 395 gga cag cca tct gcc tac ctg ccc cag gag gac tgg gcc cca ctg ggc       1249
Gly Gln Pro Ser Ala Tyr Leu Pro Gln Glu Asp Trp Ala Pro Leu Gly
400                 405                 410                 415 tct gcc agg ccc cct cct cca gac tca gac agc ggc agc agc gac tat       1297
Ser Ala Arg Pro Pro Pro Pro Asp Ser Asp Ser Gly Ser Ser Asp Tyr
                420                 425                 430 tgc atg ttg gac tgc tgt gag gaa tgc cac ctc tca gcc ttc cca gga       1345
Cys Met Leu Asp Cys Cys Glu Glu Cys His Leu Ser Ala Phe Pro Gly
            435                 440                 445 cac acc gag agt cct gag ctc acg cta gct cag cct gtg gcc ctt cct       1393
His Thr Glu Ser Pro Glu Leu Thr Leu Ala Gln Pro Val Ala Leu Pro
        450                 455                 460 gtg tcc agc agg gcc tga cacctaccaa gggatgtggg cattctcttc              1441
Val Ser Ser Arg Ala
465 cctcctatcc tcggatggca ccagacacag tctctgcgtg tctctgctag gtgcaccatg     1501 tctgttttgg ggagatgaac gaaaggcccc aggctgaccc tggggtgcgt gtggaactcc     1561 ggagaggagg cagctgtgca cggatcagag gcaatgcgga tggaagcagt agactgtgcc     1621 ttaccccccct gctctgcctt tgtggtgggg atgcctccag ggtcagcatc ttaacatccg    1681
```

```
ccttcgcttc tcttgtcttt ctggctctgt cccaggcctg aaaaaagaat gtgacaagca    1741
gcctggtctg ttcttccacc cctaaagggc tggcctgggc ccagggacac tgatgagaca    1801
acattggtga agtgtccctt ttcagtgcct ttcccattaa gaccagaagg gacgcttttg    1861
actgcaggct gtgggtggct gggtacggag ggaatgatgg agctttgagc aggtggggtt    1921
gtccatcttt gagcttttgg ggttccaaga tcagctggaa ggagtctcac cgactgattc    1981
aaagaagtct tacccatctg tgatattttc tttcctggtg ccgtgataaa acaccgtgac    2041
caaaaatgac ttacaaaagg aagagttggc ttggtttaag gttccagagg tgtggagaca    2101
tggcagccag cggcacacat ggcagtgagg acaggaagct gagagctcac atctcaacca    2161
aaagttgagt gaactgaaag tactatcccc tcccccaccc caactccagc aaggctccac    2221
cccctgaag gttccatgcc tccctaaaca gctcggccaa atagagacca agtgttcaaa    2281
tatctgagtc tgtggggac atttctcatt caaaccactt cactgccccc actgttccta    2341
ggaaaaagct gaagccaggg ctactggaca gggttggaa tggctatttc tcagcagccg    2401
gcctgtgaag aatgacgatg cccctaactg ccttctgagg tagcctggag agagctgtgg    2461
gtgggctaga atgtggctgt tattttccta ggcttgccct aacagaatac cagaaaccgg    2521
gtggctaata ccgtagattt gttttctctc tgctctgagg tccatgggtc tggaatggag    2581
acaccaggaa ggccatgctc ctggagggaa gggtttgttt ccagccctgc ttcacattcc    2641
cctctgagtg tcctcttgcg tactgagact agatgctacc caatgacggg gacaggttgt    2701
gtctcatact cttgcatgtg agcagagatt gtgacctaga aggccaaaac aggctgagca    2761
gttggccacg tttgtgcaga tttggagcca taaagcactg gcctaacaga agtcctcttg    2821
ctccttgaag ggctcttaaa gggcaagcgt gggaacaatg ctagtgtgag gactattcc    2881
aagcctgtga caccgtgcaa gagacggtcg aactactgcg cagggtccat ggagcgcaga    2941
gtccatggag cgcagagagg aactgcatgc agcattgtga gctcagagct ggtgtcctgg    3001
gaaggctcac aatgctgacc ccagg                                          3026
```

<210> SEQ ID NO 10
<211> LENGTH: 468
<212> TYPE: PRT
<213> ORGANISM: Mus musculus

<400> SEQUENCE: 10

```
Met Ala Leu Gly Arg Cys Ile Ala Glu Gly Trp Thr Leu Glu Arg Val
1               5                   10                  15

Ala Val Lys Gln Val Ser Trp Phe Leu Ile Tyr Ser Trp Val Cys Ser
            20                  25                  30

Gly Val Cys Arg Gly Val Ser Val Pro Glu Gln Gly Gly Gly Gly Gln
        35                  40                  45

Lys Ala Gly Ala Phe Thr Cys Leu Ser Asn Ser Ile Tyr Arg Ile Asp
    50                  55                  60

Cys His Trp Ser Ala Pro Glu Leu Gly Gln Glu Ser Arg Ala Trp Leu
65                  70                  75                  80

Leu Phe Thr Ser Asn Gln Val Thr Glu Ile Lys His Lys Cys Thr Phe
                85                  90                  95

Trp Asp Ser Met Cys Thr Leu Val Leu Pro Lys Glu Glu Val Phe Leu
                100                 105                 110

Pro Phe Asp Asn Phe Thr Ile Thr Leu His Arg Cys Ile Met Gly Gln
            115                 120                 125

Glu Gln Val Ser Leu Val Asp Ser Gln Tyr Leu Pro Arg Arg His Ile
```

```
                    130                 135                 140
Lys Leu Asp Pro Pro Ser Asp Leu Gln Ser Asn Val Ser Ser Gly Arg
145                 150                 155                 160

Cys Val Leu Thr Trp Gly Ile Asn Leu Ala Leu Glu Pro Leu Ile Thr
                165                 170                 175

Ser Leu Ser Tyr Glu Leu Ala Phe Lys Arg Gln Glu Glu Ala Trp Glu
            180                 185                 190

Ala Arg His Lys Asp Arg Ile Val Gly Val Thr Trp Leu Ile Leu Glu
        195                 200                 205

Ala Val Glu Leu Asn Pro Gly Ser Ile Tyr Glu Ala Arg Leu Arg Val
210                 215                 220

Gln Met Thr Leu Glu Ser Tyr Glu Asp Lys Thr Glu Gly Tyr Tyr
225                 230                 235                 240

Lys Ser His Trp Ser Glu Trp Ser Gln Pro Val Ser Phe Pro Ser Pro
                245                 250                 255

Gln Arg Arg Gln Gly Leu Leu Val Pro Arg Trp Gln Trp Ser Ala Ser
            260                 265                 270

Ile Leu Val Val Val Pro Ile Phe Leu Leu Leu Thr Gly Phe Val His
        275                 280                 285

Leu Leu Phe Lys Leu Ser Pro Arg Leu Lys Arg Ile Phe Tyr Gln Asn
290                 295                 300

Ile Pro Ser Pro Glu Ala Phe Phe His Pro Leu Tyr Ser Val Tyr His
305                 310                 315                 320

Gly Asp Phe Gln Ser Trp Thr Gly Ala Arg Arg Ala Gly Pro Gln Ala
                325                 330                 335

Arg Gln Asn Gly Val Ser Thr Ser Ala Gly Ser Glu Ser Ser Ile
            340                 345                 350

Trp Glu Ala Val Ala Thr Leu Thr Tyr Ser Pro Ala Cys Pro Val Gln
        355                 360                 365

Phe Ala Cys Leu Lys Trp Glu Ala Thr Ala Pro Gly Phe Pro Gly Leu
370                 375                 380

Pro Gly Ser Glu His Val Leu Pro Ala Gly Cys Leu Glu Leu Glu Gly
385                 390                 395                 400

Gln Pro Ser Ala Tyr Leu Pro Gln Glu Asp Trp Ala Pro Leu Gly Ser
                405                 410                 415

Ala Arg Pro Pro Pro Asp Ser Asp Ser Gly Ser Ser Asp Tyr Cys
            420                 425                 430

Met Leu Asp Cys Cys Glu Glu Cys His Leu Ser Ala Phe Pro Gly His
        435                 440                 445

Thr Glu Ser Pro Glu Leu Thr Leu Ala Gln Pro Val Ala Leu Pro Val
450                 455                 460

Ser Ser Arg Ala
465

<210> SEQ ID NO 11
<211> LENGTH: 1283
<212> TYPE: DNA
<213> ORGANISM: Homo sapiens
<220> FEATURE:
<221> NAME/KEY: CDS
<222> LOCATION: (57)..(455)

<400> SEQUENCE: 11
aagccaccca gcctatgcat ccgctcctca atcctctcct gttggcactg ggcctc atg    59
                                                              Met
                                                                1
```

```
gcg ctt ttg ttg acc acg gtc att gct ctc act tgc ctt ggc ggc ttt        107
Ala Leu Leu Leu Thr Thr Val Ile Ala Leu Thr Cys Leu Gly Gly Phe
            5                   10                  15 gcc tcc cca ggc cct gtg cct ccc tct aca gcc ctc agg gag ctc att        155
Ala Ser Pro Gly Pro Val Pro Pro Ser Thr Ala Leu Arg Glu Leu Ile
        20                  25                  30 gag gag ctg gtc aac atc acc cag aac cag aag gct ccg ctc tgc aat        203
Glu Glu Leu Val Asn Ile Thr Gln Asn Gln Lys Ala Pro Leu Cys Asn
35                  40                  45 ggc agc atg gta tgg agc atc aac ctg aca gct ggc atg tac tgt gca        251
Gly Ser Met Val Trp Ser Ile Asn Leu Thr Ala Gly Met Tyr Cys Ala
50                  55                  60                  65 gcc ctg gaa tcc ctg atc aac gtg tca ggc tgc agt gcc atc gag aag        299
Ala Leu Glu Ser Leu Ile Asn Val Ser Gly Cys Ser Ala Ile Glu Lys
                70                  75                  80 acc cag agg atg ctg agc gga ttc tgc ccg cac aag gtc tca gct ggg        347
Thr Gln Arg Met Leu Ser Gly Phe Cys Pro His Lys Val Ser Ala Gly
            85                  90                  95 cag ttt tcc agc ttg cat gtc cga gac acc aaa atc gag gtg gcc cag        395
Gln Phe Ser Ser Leu His Val Arg Asp Thr Lys Ile Glu Val Ala Gln
        100                 105                 110 ttt gta aag gac ctg ctc tta cat tta aag aaa ctt ttt cgc gag gga        443
Phe Val Lys Asp Leu Leu Leu His Leu Lys Lys Leu Phe Arg Glu Gly
115                 120                 125 cag ttc aac tga aacttcgaaa gcatcattat ttgcagagac aggacctgac           495
Gln Phe Asn
130 tattgaagtt gcagattcat ttttctttct gatgtcaaaa atgtcttggg taggcgggaa     555 ggagggttag ggaggggtaa aattccttag cttagacctc agcctgtgct gcccgtcttc     615 agcctagccg acctcagcct tccccttgcc cagggctcag cctggtgggc ctcctctgtc     675 cagggccctg agctcggtgg acccagggat gacatgtccc tacacccctc ccctgcccta     735 gagcacactg tagcattaca gtgggtgccc cccttgccag acatgtggtg ggacagggac     795 ccacttcaca cacaggcaac tgaggcagac agcagctcag gcacacttct tcttggtctt     855 atttattatt gtgtgttatt taaatgagtg tgtttgtcac cgttgggggat tggggaagac    915 tgtggctgct agcacttgga gccaaggggtt cagagactca gggccccagc actaaagcag    975 tggacaccag gagtccctgg taataagtac tgtgtacaga attctgctac ctcactgggg    1035 tcctggggcc tcggagcctc atccgaggca gggtcaggag aggggcagaa cagccgctcc   1095 tgtctgccag ccagcagcca gctctcagcc aacgagtaat ttattgtttt tccttgtatt   1155 taaatattaa atatgttagc aaagagttaa tatatagaag ggtaccttga acactggggg   1215 agggacatt gaacaagttg tttcattgac tatcaaactg aagccagaaa taaagttggt    1275 gacagata                                                            1283

<210> SEQ ID NO 12
<211> LENGTH: 132
<212> TYPE: PRT
<213> ORGANISM: Homo sapiens

<400> SEQUENCE: 12

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45
```

```
Asn Gly Ser Met Val Trp Ser Ile Asn Leu Thr Ala Gly Met Tyr Cys
    50                   55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Leu Phe Arg Glu
            115                 120                 125

Gly Gln Phe Asn
    130

<210> SEQ ID NO 13
<211> LENGTH: 1207
<212> TYPE: DNA
<213> ORGANISM: Mus musculus
<220> FEATURE:
<221> NAME/KEY: CDS
<222> LOCATION: (70)..(465)

<400> SEQUENCE: 13
gacaagccag cagcctaggc cagcccacag ttctacagct ccctggttct ctcactggct    60 ctgggcttc atg gcg ctc tgg gtg act gca gtc ctg gct ctt gct tgc ctt   111
           Met Ala Leu Trp Val Thr Ala Val Leu Ala Leu Ala Cys Leu
               1               5                   10 ggt ggt ctc gcc gcc cca ggg ccg gtg cca aga tct gtg tct ctc cct    159
Gly Gly Leu Ala Ala Pro Gly Pro Val Pro Arg Ser Val Ser Leu Pro
15                  20                  25                  30 ctg acc ctt aag gag ctt att gag gag ctg agc aac atc aca caa gac    207
Leu Thr Leu Lys Glu Leu Ile Glu Glu Leu Ser Asn Ile Thr Gln Asp
                35                  40                  45 cag act ccc ctg tgc aac ggc agc atg gta tgg agt gtg gac ctg gcc    255
Gln Thr Pro Leu Cys Asn Gly Ser Met Val Trp Ser Val Asp Leu Ala
            50                  55                  60 gct ggc ggg ttc tgt gta gcc ctg gat tcc ctg acc aac atc tcc aat    303
Ala Gly Gly Phe Cys Val Ala Leu Asp Ser Leu Thr Asn Ile Ser Asn
        65                  70                  75 tgc aat gcc atc tac agg acc cag agg ata ttg cat ggc ctc tgt aac    351
Cys Asn Ala Ile Tyr Arg Thr Gln Arg Ile Leu His Gly Leu Cys Asn
    80                  85                  90 cgc aag gcc ccc act acg gtc tcc agc ctc ccc gat acc aaa atc gaa    399
Arg Lys Ala Pro Thr Thr Val Ser Ser Leu Pro Asp Thr Lys Ile Glu
95                  100                 105                 110 gta gcc cac ttt ata aca aaa ctg ctc agc tac aca aag caa ctg ttt    447
Val Ala His Phe Ile Thr Lys Leu Leu Ser Tyr Thr Lys Gln Leu Phe
                115                 120                 125 cgc cac ggc ccc ttc taa tgaggagaga ccatccctgg gcatctcagc           495
Arg His Gly Pro Phe
            130 tgtggactca ttttcctttc tcacatcaga ctttgctggg gagaggcagg gaggagggtt   555 gaggaggaag ggagatgcct cagctttggc ctcagcctgc actgcctgcc tagtgctcag   615 ggtctcagcc tggcaacacc cccacccac cccacccccc gccgcccat cccatcccta    675 cagaaaactg cagcaagacc gtgagtccag cctgtggcct ggtccacaca gggcaactga   735 ggcaggcagc agcttgagca catttcttct tgatcttatt tattatggtt gtgtgttatt   795 taaatgagtc tgtcagtatc ccggtgggga catggtttgc tgcctatgcc ctgggggctc   855
```

```
cagcattgaa gcagtgggct ctggggtccc tggcaatatt actgtataca taactctgct    915
acctcactgt agcctccagg tctcacccca ggcaggagaa tgggagggga ggccagagca    975
acactcctgt ctgccacggc agcaaccagc cctcagccat gaaataactt attgttttgt   1035
tcttatattt aaagtattaa atagcttagc aaagagttaa taatatatgg aagaatggcc   1095
tgttacactc aaggtgatgt gtagtgaatg gggggagggt ggtgggtttg tcactgaaca   1155
aacttttcat tgactgtcaa actagaaacc ggaaataaag atggtgacag at           1207
```

<210> SEQ ID NO 14
<211> LENGTH: 131
<212> TYPE: PRT
<213> ORGANISM: Mus musculus

<400> SEQUENCE: 14

Met Ala Leu Trp Val Thr Ala Val Leu Ala Leu Ala Cys Leu Gly Gly
1               5                   10                  15

Leu Ala Ala Pro Gly Pro Val Pro Arg Ser Val Ser Leu Pro Leu Thr
            20                  25                  30

Leu Lys Glu Leu Ile Glu Glu Leu Ser Asn Ile Thr Gln Asp Gln Thr
        35                  40                  45

Pro Leu Cys Asn Gly Ser Met Val Trp Ser Val Asp Leu Ala Ala Gly
    50                  55                  60

Gly Phe Cys Val Ala Leu Asp Ser Leu Thr Asn Ile Ser Asn Cys Asn
65                  70                  75                  80

Ala Ile Tyr Arg Thr Gln Arg Ile Leu His Gly Leu Cys Asn Arg Lys
                85                  90                  95

Ala Pro Thr Thr Val Ser Ser Leu Pro Asp Thr Lys Ile Glu Val Ala
            100                 105                 110

His Phe Ile Thr Lys Leu Leu Ser Tyr Thr Lys Gln Leu Phe Arg His
        115                 120                 125

Gly Pro Phe
    130

<210> SEQ ID NO 15
<211> LENGTH: 18
<212> TYPE: PRT
<213> ORGANISM: Artificial
<220> FEATURE:
<223> OTHER INFORMATION: Synthetic peptide sequence

<400> SEQUENCE: 15

Ser Asp Asn Ala Thr Arg Pro Ala Phe Ser Glu Arg Leu Ser Gln Met
1               5                   10                  15

Thr Asn

<210> SEQ ID NO 16
<211> LENGTH: 18
<212> TYPE: PRT
<213> ORGANISM: Artificial
<220> FEATURE:
<223> OTHER INFORMATION: Synthetic peptide sequence

<400> SEQUENCE: 16

Phe Ser Arg Val Lys Lys Ser Val Glu Val Leu Lys Asn Asn Lys Ala
1               5                   10                  15

Pro Tyr

<210> SEQ ID NO 17
<211> LENGTH: 18

```
<212> TYPE: PRT
<213> ORGANISM: Artificial
<220> FEATURE:
<223> OTHER INFORMATION: Synthetic peptide sequence

<400> SEQUENCE: 17

Glu Gln Pro Ala Asn Gln Thr Thr Ala Gly Asn Ala Leu Thr Phe Leu
1               5                   10                  15

Lys Ser

<210> SEQ ID NO 18
<211> LENGTH: 18
<212> TYPE: PRT
<213> ORGANISM: Artificial
<220> FEATURE:
<223> OTHER INFORMATION: Synthetic peptide sequence

<400> SEQUENCE: 18

Thr Ala Gly Asn Ala Leu Thr Phe Leu Lys Ser Leu Leu Glu Ile Phe
1               5                   10                  15

Gln Lys
```

METHODS FOR THE MODULATION OF IL-13

This application is a divisional of U.S. patent application Ser. No. 10/479,870, filed Jun. 2, 2004 (now abandoned), which is a §371 National Stage Application of PCT Application No. PCT/US02/17881 with an international filing date of Jun. 10, 2002, and claims the benefit of U.S. provisional application 60/297,190, filed Jun. 8, 2001 which are herein incorporated by reference in their entirety.

A computer readable text file, entitled "SeqListing.txt," created on or about Mar. 18, 2009 having a size of about 42.7 kb contains the sequence listing for this application and is hereby incorporated by reference.

FIELD OF THE INVENTION

This invention relates to modulation of the IL-13 expression and activity in a mammal though modulation of IL-9 expression and activity.

BACKGROUND OF THE INVENTION

Interleukin-13 (IL-13) is a cytokine expressed in inflammatory immune responses that are controlled by Th2-type T lymphocytes (Minty et al. (1993) Nature 362, 248-250; McKenzie et al. (1993) Proc. Natl. Acad. Sci. USA 90, 3735-3739). Recently it has been suggested that IL-13 plays a central role in the pathogenesis of asthma (Wills-Karp et al. (1998) Science 282, 2258-2261; Grunig et al. (1998) Science 282, 2261-2263) and transgenic expression of IL-13 in the lung produced an asthmatic like response (Zhu et al. (1999) J. Clin. Invest. 103, 779-788). IL-13 expression is also found to be elevated in asthma patients (Walker et al. (1992) Am. Rev. Respir. Dis. 146, 109-115; Humbert et al. (1997) J. Allergy Clin. Immunol. 99, 657-665; Huang (1995) J. Immunol. 155, 2688-2694) and asthma has been genetically linked to chromosome 5q, a region that contains both the IL-13 and the IL-9 genes (Marsh et al. (1996) Science 264, 1152-1156).

Based on the data presented in the patent applications listed above, there is substantial support for the role of the cytoline IL-9 in the pathogenesis of asthma. First, applicants demonstrate linkage homology between humans and mice, suggesting the same gene is responsible for producing biologic variability in response to antigen in both species. Second, differences in expression of the murine IL-9 candidate gene are associated with biologic variability in bronchial responsiveness. In particular, reduced expression of IL-9 is associated with a lower baseline bronchial response in B6 mice. Third, recent evidence for linkage disequilibrium in data from humans suggests IL-9 may be associated with atopy and bronchial hyperresponsiveness consistent with a role for this gene in both species (Doull et al. (1996) Am. J. Respir. Crit. Care Med. 153, 1280-1284). Moreover, applicants have demonstrated that a genetic alteration in the human gene appears to be associated with loss of cytokine function and lower IgE levels. Fourth, the pleiotropic functions of this cytokine and its receptor in the allergic immune response strongly support a role for the IL-9 pathway in the complex pathogenesis of asthma. Fifth, in humans, biologic variability in the IL-9 receptor also appears to be associated with atopic allergy and asthma. Finally, despite the inherited loss of IL-9 receptor function, these individuals appear to be otherwise healthy. Thus, nature has demonstrated in atopic individuals that the therapeutic down-regulation of IL-9 and IL-9 receptor genes or genes activated by IL-9 and its receptor is likely to be safe and useful for the treatment of asthma.

In some infectious diseases it has recently been suggested that elevated levels of IL-13 may contribute to the pathogenesis of the disease. For example, in patients with tuberculosis it has been demonstrated that there is a very large relative increase in IL-4 and IL-13 expression, that correlates with lung damage and indicates that a T helper-2 (Th2) component in the response to *M. tuberculosis* may undermine the efficacy of immunity and contribute to immunopathology (Rook et al. (2001) Curr. Opin. Pulm. Med. 7, 116-123). In addition, in patients with dengue hemorrhagic fever it has been suggested that high levels of IL-13 may contribute to the shift from a Th1 to Th2 type response and thus to the pathogenesis of the disease (Mustafa et al. (2001) FEMS Immunol. Med. Microbiol. 30, 229-233).

High levels of IL-13 have also associated with diseases that are characterized by fibrosis (Oriente et al. (2000) J. Pharmacol. Exp. Ther. 292, 988-994), for example Hodgkin's disease (Ohshima et al. (2001) Histopathology 38, 368-375).

IL-13 has also been shown to be capable of up-regulating the enzyme 15-lipoxygnase and the down-regulation of its isozyme 5-lipoxygenase (Nassar et al. (1994) J. Biol. Chem. 269, 27631-27634; Spanbroek et al. (2001) Proc. Natl. Acad. Sci. USA 98, 5152-5157). The net effect appears to be the down-regulation of a Th1 mediated inflammatory response.

It has previously been shown that IL-9 is important in asthma and other inflammatory diseases. The present invention is based, in part, upon the discovery described herein that control IL-9 levels can be utilized to control IL-13 levels in inflammatory diseases such as asthma.

SUMMARY OF THE INVENTION

The present invention is drawn to a method for modulating IL-13 expression and/or activity in a mammal, preferably a human, comprising administering an effective amount of an agent which modulates the expression and/or activity of IL-9. In a preferred embodiment IL-13 expression and/or activity is down-regulated.

In some embodiments of the invention the agent is an IL-9 antagonist. In a preferred embodiment the IL-9 antagonist is an antibody against IL-9 or the IL-9 receptor. In a further embodiment thereof, the antibody is a monoclonal antibody. In a preferred embodiment the antibody is a chimeric antibody and in a specific embodiment thereof, the chimeric antibody is a humanized antibody. In another embodiment the IL-9 antagonist is a soluble IL-9 receptor protein.

In a preferred embodiment the down-regulation of IL-13 alleviates at least one symptom associated with an atopic allergy and in a particularly preferred embodiment the atopic allergy is asthma. Examples of symptoms which can be alleviated by the method of the present invention include, but are not limited to, bronchial hyperresponsiveness, bronchoconstriction, bronchial inflammation, pulmonary fibrosis, eosinophilia, elevated serum IgE levels and mucin overproduction. In another embodiment, the down-regulation of IL-13 produces a down-regulation in 15-lipoxygenase expression and/or activity, or an up-regulation in isozyrne 5-lipoxygenase expression and/or activity.

The present invention is also drawn to treating a disease associated with elevated levels of IL-13 in a mammal, preferably a human, comprising administration of an effective amount of an IL-9 antagonist. In a preferred embodiment the disease is an atopic allergy and in a particularly preferred embodiment the atopic allergy is asthma. In another preferred embodiment the disease is an infectious disease. In a specific embodiment, the disease is further associated with a Th1-type inflammatory response. In a preferred embodiment the IL-9 antagonist is an antibody against IL-9 or the IL-9 receptor. In a further embodiment thereof, the antibody is a monoclonal antibody. In a preferred embodiment the antibody is a chimeric antibody and in a specific embodiment thereof, the chimeric antibody is a humanized antibody. In another embodiment the IL-9 antagonist is a soluble IL-9 receptor protein.

In some embodiments of the present invention, the agent is administered by a route selected from the group consisting of intravenous, subcutaneous, transdermal, mucosal, intranasal, oral, bronchial administration. In a particular embodiment, the bronchial administration is carried out with an aerosol inhaler.

Another aspect of the present invention is a method of identifying an agent which modulates IL-13 expression and/or activity comprising contacting a cell expressing an IL-9 receptor with the agent in the presence of an IL-9 receptor ligand, and measuring the expression and/or activity of IL-13, wherein a decrease in IL-13 expression and/or activity indicates an agent capable of modulating IL-13 expression and/or activity. In some embodiments, the IL-9 receptor ligand is selected from the group consisting of IL-9 or a fragment thereof, an IL-9 analog and an IL-9 peptide mimetic.

DETAILED DESCRIPTION OF THE INVENTION

General Description

Figure 1:
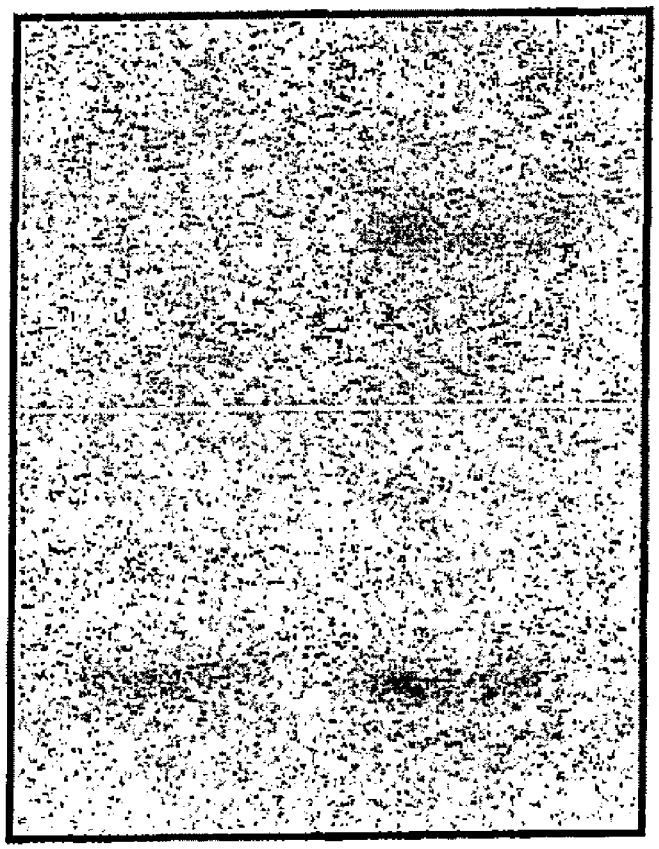
FIG. 1 depicts induction of IL-13 gene expression in transgenic mice overexpressing IL-9.

The invention is based on the identification of IL-13 in the IL-9 pathway and methods for regulating the pathway which may be used in the treatment of diseases associated with IL-13.

The invention includes methods of modulating IL-13 expression and/or activity by treating a subject with an agent which modulates the expression and/or activity of IL-9. Agents of the invention may be an anti-IL-9 antibody or anti-IL-9 receptor antibody, particularly a neutralizing antibody, soluble IL-9 receptor or fragments thereof, fragments of IL-9 which competitively inhibit IL-9 binding to the receptor, analogs of IL-9, and peptide mimetics of IL-9. The modulation of IL-13 is useful for the treatment of atopic allergies, including asthma. Methods for modulation of IL-13 are further useful for the treatment of infectious diseases.

Modulation of IL-13 Expression and/or Activity

IL-13 has been identified as a cytokine protein that is associated with IL-9 and subsequent activity of a Th1-type immune response leading to inflammation. Specifically, the expression and activation of IL-13 is dependent upon the expression and activity of IL-9. The present invention therefore includes methods for modulating IL-13 expression and/or activity by modulating IL-9 expression and/or activity, including methods for modulating IL-9 signal transduction pathways via downstream membrane and cytoplasmic signaling proteins, to effect activation of a Th1-type immune response. Such methods will be useful in the treatment of disorders associated with diseases associated with a Th1-type immune responses. Because IL-9 receptor expression and activity also indirectly effects IL-13 expression and activity via a general feedback mechanism, the invention also includes methods for modulating IL-13 expression and activity by modulating IL-9 receptor expression and/or activity.

Modulation of the IL-9 and/or IL-9 receptor gene, gene fragments, or the encoded protein or protein fragments is useful in gene therapy to treat disorders associated with IL-13 defects. For increased expression of IL-13, expression of IL-9 and/or its receptor is increased. Expression vectors may be used to introduce IL-9 or the IL-9 receptor gene into a cell. In a preferred embodiment, IL-9 expression is decreased to decrease IL-13 expression and activity in diseases associated with Th1-type immune responses and inflammation. Expression vectors may be used to introduce inactive, variant forms of IL-9 or the IL-9 receptor gene into a cell as has been demonstrated with mutated, inactive forms of IL-9 and the IL-9 receptor with any of the mutations described in U.S. Pat. No. 6,037,149 or U.S. patent application Ser. No. 09/596,377 (these references herein incorporated by reference in their entirety). Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid, retrovirus, lentivirus, adenovirus and the like, where the vectors are able to transiently or stably be maintained in the cells, usually for a period of at least about one day, more usually for a period of at least about several days to several weeks.

Both active and inactive, variant forms of IL-9 gene or the IL-9 receptor gene or proteins may be introduced into tissues or host cells by any number of routes, including viral infection, microinjection, or fusion of vesicles. Jet injection may also be used for intramuscular administration, as described by Furth et al. (1992) Anal. Biochem. 205, 365-368. The DNA may be coated onto gold microparticles, and delivered intradermally by a particle bombardment device, or using a "gene gun", as described in the literature (see, for example, Tang et al. (1992) Nature 356, 152-154), where gold microprojectiles are coated with mutant IL-9 receptor DNA, then bombarded into skin cells.

In a further embodiment, the invention includes the down-regulation of IL-13 expression and/or activity by administering soluble IL-9 receptor protein that binds IL-9 (Renauld et al. (1992) Proc. Natl. Acad. Sci. USA 89, 5690-5694). These soluble proteins can be used to prevent the binding of IL-9 to cell bound receptor and act as an antagonist of IL-9. Soluble receptors have been used to bind cytokines or other ligands to regulate their function (Thomson (1998) Cytokine Handbook, Academic Press). A soluble receptor is a form of a membrane bound receptor that occurs in solution, or outside of the membrane. Soluble receptors may occur because the segment of the molecule which commonly associates with the membrane is absent. This segment is commonly referred to in the art as the transmembrane domain of the gene, or membrane binding segment of the protein. Thus, in one embodiment of the invention, a soluble receptor may represent a fragment or an analog of a membrane bound receptor. In another embodiment of the invention, the structure of the segment that associates with the membrane may be modified (e.g., DNA sequence polymorphism or mutation in the gene) so the receptor is not inserted into the membrane, or the receptor is inserted, but is not retained within the membrane. Thus, a soluble receptor, in contrast to the corresponding membrane bound form, differs in one or more segments of the gene or receptor protein that are important to its association with the membrane (Renauld et al., (1992) Proc. Natl. Acad. Sci. USA 89, 5690-5694; Chang et al. (1994) Blood 83, 3199-3205).

These soluble receptors may be known forms of a soluble IL-9 receptor that act to bind IL-9. Alternatively, these soluble receptors may contain variations but still resemble known forms of the IL-9 receptor, and may exist as fragments. Examples of variant soluble IL-9 receptors and fragments thereof can be found in U.S. Pat. No. 6,037,149 and U.S. patent application Ser. No. 09/596,377 (these references herein incorporated by reference in their entirety). In another embodiment of the invention, the compound may retain functions comparable to soluble IL-9 receptor, but may not resemble soluble IL-9 receptor in composition. For example, the composition of the compound may include molecules other than amino acids. Thus, these compounds will bind IL-9 and prevent IL-9 from acting at its cell surface receptor.

Antisense molecules can be used to down-regulate expression of IL-9 or IL-9 receptor expression in cells. The antisense reagent may be antisense oligonucleotides, particularly synthetic antisense oligonucleotides having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g., by reducing the amount of mRNA available for translation, through activation of RNAseH or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will range from five to seventy-five and generally be at least about seven, usually at least about twelve, and more usually at least about twenty nucleotides in length. Typical antisense oligonucleotides are usually not more than about five-hundred, more usually not more than about fifty, and even more usually not more than about thirty-five nucleotides in length, where the length is governed by efficiency of inhibition, specificity, including absence of cross-reactivity, and the like. It has been found that short oligonucleotides, from seven to eight bases in length, can be strong and selective inhibitors of gene expression (see Wagner et al. (1996) Nat. Biotech. 14, 840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1996) Nat. Biotech. 14, 840-844). Preferred oligonucleotides are chemically modified from the native phosphodiester structure, in order to increase their intracellular stability (e.g., resistance to nuclease degradation and acid resistance) and binding affinity. A number of such modifications have been described in the literature, which alter the chemistry of the backbone, sugars or heterocyclic bases.

As an alternative to anti-sense inhibitors, catalytic nucleic acid compounds, e.g., ribozymes, deoxyribozymes (see, for example, Santoro et al. (1997) Proc. Natl. Acad. Sci. USA 94, 4262-4266), anti-sense conjugates, etc. may be used to inhibit gene expression. Ribozymes may be synthesized in vitro and administered to the patient, or may be encoded on an expression vector, from which the ribozyme is synthesized in the targeted cell (see, for example, WO 95/23225; Beigelman et al. (1995) Nuc. Acids Res. 23, 4434-4442). Examples of oligonucleotides with catalytic activity are described in WO 95/06764.

Methods of Treatment Associated with Modulation of IL-13 Expression

As provided in the Examples, the IL-13 protein and nucleic acid are expressed in response to stimulation by IL-9. Agents that modulate or up- or down-regulate the expression of the IL-9 protein or agents such as agonists or antagonists of at least one activity of the IL-9 or IL-9 receptor protein may be used to modulate biological, and pathologic processes associated with IL-13 function and activity in a subject. As used herein, a "subject" can be any mammal, so long as the mammal is in need of modulation of a pathological or biological process mediated by a protein of the invention. The term "mammal" is defined as an individual belonging to the class Mammalia. The invention is particularly useful in the treatment of human subjects.

Pathological processes refer to a category of biological processes which produce a deleterious effect. For example, increased IL-13 expression and/or activity is associated with diseases characterized by a Th1-type immune response leading to inflammation. Such diseases include, but are not limited to, atopic allergy. As used herein, the term "atopic allergy" refers to atopy and related disorders including asthma, bronchial hyperresponsiveness, rhinitis, urticaria, allergic inflammatory disorders of the bowel and various forms of eczema. Atopy is a hypersensitivity to environmental allergens expressed as the elevation of serum total IgE or abnormal skin test responses to allergens as compared to controls. Atopic allergies include conditions where there is a genetic predisposition toward the development of immediate (type I) hypersensitivity reactions against common environmental antigens. Bronchial hyperresponsiveness is characterized by a heightened broncheconstrictor response to a variety of external stimuli.

Modulation of IL-13 expression can therefore be used to treat different types of atopic allergy and symptoms associated with types of atopic allergy. Symptoms of atopic allergy include, but are not limited to, bronchial hyperresponsiveness, bronchoconstriction, bronchial inflammation, pulmonary fibrosis, eosinophilia, elevated serum IgE levels and mucin overproduction. Examples of atopic allergy treatable by the present method include, but are not limited to, allergic rhinitis, bronchial asthma, atopic dermatitis, food allergies, allergies to animal dander or products, pollen allergies, and dust allergies.

As discussed above, those skilled in the art will appreciate that a wide variety of conditions are associated with IL-9 dependent increases in IL-13 expression and/or activity. Asthma is an example of one such atopic allergy characterized by increased IL-13 expression and/or activity associated with IL-9. As used herein, the term "asthma" encompasses inflammatory disorders of the airways with reversible airflow obstruction. The term further refers to conditions marked by recurrent attacks of paroxysmal dyspnea, with wheezing due to spasmodic contraction of the bronchii. Some cases of asthma are allergic manifestations in sensitized persons (bronchial allergy); others are provoked by a variety of factors including, but not limited to, exercise, irritant particles, animal dander, pollen, and psychological stress. Symptoms of asthma include, but are not limited to, bronchial hyperresponsiveness, bronchoconstriction, bronchial inflammation, pulmonary fibrosis, eosinophilia, elevated serum IgE levels and mucin overproduction.

As used herein, an agent is said to modulate a pathological process when the agent reduces the degree or severity of the process. For instance, a disorder associated with IL-13 expression may be prevented or disease progression modulated by the administration of agents which reduce, promote or modulate in some way the expression or at least one activity of IL-9 or its receptor. For atopic allergy, including asthma, the therapeutic strategy comprises a treatment with the agent until the aforementioned symptoms associated with atopic allergy, including asthma, are alleviated. Then the treatment can be switched to established regimens for the prevention of atopic allergy, including asthma, to avoid potential side effects of IL-13 levels which are below normal.

Other embodiments of the present invention allow for the treatment of other conditions that involve IL-13 expression. For example, many types of infectious disease are associated with elevated levels of IL-13. High levels of IL-13 have also associated with diseases that are characterized by fibrosis such as Hodgkin's disease. A decrease in IL-13 expression and/or activity through inhibition of IL-9 can be useful to decrease Th1-type immune responses associated with these diseases. Organisms responsible for, or contributing to, infectious diseases treatable by the present methods include, but are not limited to, viruses, bacteria, protozoa, fungi, and parasites. Examples of infectious disease include, but are not limited to, myobacterium tuberculosis, hemorrhagic fever, etc.

The invention also includes pharmaceutical compositions comprising the agents of the invention together with a pharmaceutically acceptable carrier. Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in Remington's Pharmaceutical Sciences, Mack Publishing (1995).

The agents used in the method of treatment of this invention may be administered systemically, topically or enterally, depending on such considerations as the condition to be treated, need for site-specific treatment, quantity of drug to be administered and similar considerations. Indeed, all three types of formulations may be used simultaneously to achieve systemic administration of the active ingredient.

Topical administration may be used. Any common topical formation, such as a solution, suspension, gel, ointment or salve and the like may be employed. Preparation of such topical formulations are well described in the art of pharmaceutical formulations as exemplified, for example, by Gennaro et al. (1995) Remington's Pharmaceutical Sciences, Mack Publishing. For topical application, these agents could also be administered as a powder or spray, particularly in aerosol form. The active ingredient may be administered in pharmaceutical compositions adapted for systemic administration. As is known, if a drug is to be administered systemically, it may be confected as a powder, pill, tablet or the like or as a syrup or elixir for oral administration. Preparations for oral administration may be suitably formulated to give controlled release of the active compound.

The agents used in the method of treatment of this invention may be formulated for parenteral administration by injection, e.g., by bolus injection or continuous infusion. As used herein, the term "parenteral" refers to routes of administration including, but not limited to, intravenous, intraperitoneal, intra-lesional, subcutaneous, intradermal, intramuscular, intracapsular, and direct injection into mucosal tissues. Formulations for injection may be presented in unit dosage form, e.g., in ampoules or in multi-dose containers. The agents may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In some embodiments, the agents may also be formulated in rectal compositions such as suppositories or retention enemas, e.g., containing conventional suppository bases such as cocoa butter or other glycerides. In some embodiments, the agents may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

In some embodiments of the present invention, the route of administration of agents for use in the present invention is in an aerosol or inhaled form administered using any appropriate inhaler, insufflator or inhalation device known in the art including, but not limited to, a nebulizer, a pressurized metered dose inhaler (MDI), or a dry powder inhaler, for example. The agents can be administered as dry powder particles or as an atomized aqueous solution suspended in a carrier gas. In a related embodiment, the invention includes administration by bronchial lavage, wherein the agent in instilled in an effective amount in the fluid to be administered to the lungs via lavage.

Dry aerosol in the form of finely divided solid particles of agents for use according to the present invention that are not dissolved or suspended in a liquid can be administered using a dry powder inhaler, such as those well known in the art. The agent may be in the form of dusting powders and comprise finely divided particles having an average particle size of between about 1 and 5 microns, preferably between 2 and 3 microns. Finely divided particles may be prepared by pulverization and screen filtration using techniques well known in the art. Capsules and cartridges of, e.g., gelatin for use in an inhaler or insufflator may be formulated containing a powder mix of the compound and a suitable powder base, e.g., lactose or a starch. The particles may be administered by inhaling a predetermined quantity of the finely divided material, which can be in the form of a powder.

Agents for use according to the present invention may be administered comprised in pharmaceutical formulations in the form of an aerosol spray using for example, a nebulizer, wherein the agent is dispersed as an atomized aqueous solution suspended in a carrier gas (e.g., air, $N_2$, $CO_2$, dichlorodifluoromethane, trichlorofluoromethane, dichlorotetrafluoroethane, or other suitable gas) and the aerosol material is inhaled by the subject to be treated. Preferred aerosol pharmaceutical formulations may comprise for example, a physiologically-acceptable buffered saline solution containing between about 1 mg and about 300 mg of the antigens. Specific non-limiting examples of the carriers and/or diluents that are useful in the by -inhalation pharmaceutical formulations include water and physiologically-acceptable buffered solutions such as cromolyn sodium or phosphate buffered saline solutions pH 7.0-8.0.

As used herein, an "effective amount" of an agent of the invention is that amount which will change the level of IL-13. Preferably, an effective amount is that amount which will significantly change the level of IL-13. Also preferably, an effective amount is that amount which will change the level of IL-13 by at least about ten percent, more preferably by at least about twenty percent, even more preferably by at least about thirty percent, yet more preferably by at least about forty percent, still more preferably by at least about fifty percent, even still more preferably by at least about sixty percent, yet still more preferably by at least about seventy percent, still further more preferably by at least about eighty percent, yet further more preferably by at least about ninety percent, and in a particularly preferable embodiment by at least about ninety-five percent. Most preferably, an effective amount is that amount which will change the level of IL-13 by at least about ninety-nine percent. A given effective amount will vary from condition to condition and in certain instances may vary with the severity of the condition being treated and the patient's susceptibility to treatment. Accordingly, a given effective amount will be best determined at the time and place through routine experimentation. However, it is anticipated that in the treatment of atopic allergy and asthma-related disorders and other diseases, in accordance with the present invention, a formulation containing between 0.001 and 5.0 percent by weight, preferably about 0.01 to 1.0 percent, will usually constitute a therapeutically effective amount. When administered systemically, an amount between 0.01 and 100 milligrams per kilogram body weight per day, but preferably about 0.1 to 10 milligrams per kilogram, will effect a therapeutic result in most instances.

In practicing the methods of this invention, the agents of the invention may be used alone or in combination, or in combination with other therapeutic or diagnostic agents. In certain preferred embodiments, the agents of the invention may be co-administered along with other compounds typically prescribed for conditions according to generally accepted medical practice. For example, an agent of the present invention can be administered in combination with other drugs for the treatment of atopic allergy, including asthma, related disorders, or other drugs for the treatment of infective diseases. As used herein, two agents are said to be administered in combination when the two agents are administered simultaneously or are administered independently in a fashion such that the agents will act at the same time. The agents of this invention can be utilized in vivo in mammals, such as humans, sheep, horses, cattle, pigs, dogs, cats, rats and mice, or in vitro.

The present invention also includes antagonists of IL-9 and its receptor, such as disclosed in U.S. Pat. No. 6,261,559 (herein incorporated by reference in its entirety). In particularly preferred embodiments, an antagonist of IL-9 or its receptor is an agent that, though its effect on the IL-9 pathway, inhibits the up-regulation of IL-13 expression in response to a stimulus. Antagonists are compounds that cause effects by preventing the action of an agonist. IL-9 antagonists of the present invention include, but are not limited, neutralizing antibodies to IL-9, antibodies to IL-9 receptor, agents which competitively bind to the IL-9 receptor without activation of the receptor, soluble forms of the IL-9 receptor, and fragments of the IL-9 receptor which prevent IL-9 binding to IL-9 receptor. These and further antagonists of the invention may be tested for competitive binding with a known agonist, or for down-regulation of IL-9-like functions as described in U.S. Pat. No. 6,261,559 and the references cited therein. The binding of either the agonist or antagonist may involve all known types of interactions including ionic forces, hydrogen bonding, hydrophobic interactions, van der Waals forces, and covalent bonds. In many cases, bonds of multiple types are important in the interaction of an agonist or antagonist with a receptor.

In a further embodiment, agents of the invention may be analogs of IL-9. Such analogs may be produced by point mutations in the isolated DNA sequence for the gene, nucleotide substitutions, and/or deletions which can be created by methods that are all well described in the art (see, e.g., Simoncsits et al. (1994) Cytokine 6, 206-214). This invention also includes splice variants of IL-9 which contain deletions of one or more of its five exons as disclosed in related U.S. Pat. No. 6,261,559. The term "splice variants" as used herein denotes a purified and isolated DNA molecule encoding human IL-9 comprising at least one exon. There is no evidence of naturally expressed spliced mutants in the art. Thus, the agents of the present invention can include a protein encoded by an isolated nucleic acid containing exons 1, 4 and 5 of human IL-9. Other variants within the scope of this invention include sequences comprising exons 1, 2, 3, 4 and 5; exons 1, 2, 3 and 4; exons 1, 2, 4 and 5 and exons 1, 3, 4 and 5. It is understood that these exons may contain various point mutations.

Specific examples of antagonistic peptides derived from IL-9 include KP-16 (SEQ ID NO: 15) and KP-20 (SEQ ID NO: 16) which are derived from exon 4. Exon 4 encodes forty-four amino acids while the peptides mentioned above contain sixteen and twenty amino acids respectively and they do not overlap. These peptides exhibit considerable inhibitory activity both individually and when assayed in combination. Additionally, KP-23 (SEQ ID NO: 17) and KP-24 (SEQ ID NO: 18) are derived from exon 5 and also exhibit similar activity. The sequences of KP-16, KP-20, KP-23 and KP-24 are disclosed in U.S. Pat. No. 6,037,149 (herein incorporated by reference in its entirety). Splice variants of IL-9 can be formed by deletion of any one or more of the IL-9 exons 1 through 5. As shown above, peptides derived from these exons show regulatory capability and, accordingly, are useful in treating atopic allergies, including asthma.

In another embodiment, the agents of the invention are antibodies to IL-9 or the IL-9 receptor. As used herein, the term "antibody" refers to immunoglobulins and is used in the broadest sense, including monoclonal antibodies, polyclonal antibodies, multispecific antibodies (e.g., bispecific antibodies) and antibody fragments. An antibody is said to "recognize" an epitope if it binds to the epitope. Hence, "recognition" involves the antibody binding reaction with an epitope, which may include the typical binding mechanisms and methods. "Binding" is thus used in the conventional sense, and does not require the formation of chemical bonds.

As used herein, the term "antibody fragments" refers to a portion of a full length antibody capable of binding an epitope, generally the antigen binding or variable region thereof. Examples of antibody fragments include Fab, Fab' and F(ab')$_2$ or Fv fragments; diabodies; linear antibodies; single-chain antibody molecules; and multispecific antibodies formed from antibody fragments.

As used herein, the term "monoclonal antibody" refers to an antibody obtained from a population of substantially homogeneous antibodies (i.e., the individual antibodies comprising the population are identical except for possible naturally occurring mutations that may be present in minor amounts). Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256, 495-497 or may be made by recombinant DNA methods (see, e.g., U.S. Pat. No. 4,816,567). The monoclonal antibodies may also be isolated from phage antibody libraries using the techniques described in, for example, Clackson et al. (1991) Nature 352, 624-628 and Marks et al. (1991) J. Mol. Biol. 222, 581-597.

Monoclonal antibodies specifically include "chimeric" antibodies (immunoglobulins) in which a portion of the heavy and/or light chain is identical with, or homologous to corresponding sequences in antibodies derived from a particular species, or belonging to a particular antibody class or subclass, while the remainder of the chain(s) is identical with, or homologous to corresponding sequences in antibodies derived from another species or belonging to another antibody class or subclass, as well as fragments of such antibodies (see, e.g., U.S. Pat. No. 4,816,567 and Morrison et al. (1984) Proc. Natl. Acad. Sci. USA 81, 6851-6855). Chimeric antibodies also include "humanized" antibodies, as well as fragments of such antibodies, wherein the antigen-recognized sites, or complementarily-determining hypervariable regions (CDR) are of non-human origin, whereas framework regions (FR) of variable domains and constant regions are products of human genes. Said CDR and FR regions may comprise amino-acid alterations in order to adjust the binding affinity of the humanized antibody (see, e.g., Gussow et al. (1991) Meth. Enzymol. 203, 99-121).

The antibodies to IL-9 and the IL-9 receptor may be either monoclonal or polyclonal made using standard techniques well known in the art (Harlow & Lane (1988) Antibodies, A Laboratory Manual, Cold Spring Harbor Laboratory Press). They can be used to block IL-9 from binding to the receptor. In one embodiment the antibodies interact with IL-9. In another embodiment the antibodies interact with the IL-9 receptor. The IL-9 used to elicit these antibodies can be any of the IL-9 variants discussed above. Antibodies are also produced from peptide sequences of IL-9 or the IL-9 receptor using standard techniques in the art (Harlow & Lane (1988) Antibodies, A Laboratory Manual, Cold Spring Harbor Laboratory Press). Examples of peptide sequences from the IL-9 receptor that can be used to produce blocking antisera are disclosed in U.S. Pat. No. 6,037,149. IL-9 and IL-9 receptor sequences comprising epitopes from murine sequences are also useful for the production of therapeutic antibodies.

In another aspect of the invention, aminosterol compounds are also useful in the inhibition of signal transduction due to IL-9 stimulation. Specifically, aminosterol compounds can be used to down-regulate IL-9 expression and/or activity leading to a decrease in IL-13 expression and/or activity. Aminosterol compounds which are useful in this invention are described in U.S. Pat. No. 5,637,691 and its related U.S. Pat. Nos. 5,733, 899 and 5,721,226 as well as in U.S. Pat. No. 5,840,740 and its related U.S. Pat. Nos. 5,795,885; 5,994,336; 5,763,430; 5,840,936; 5,874,597; 5,792,635 and 5,847,172 (which are specifically incorporated herein by reference in their entirety).

Screening for Agents which Modulate IL-13 Expression

Another embodiment of the present invention provides methods for identifying agents that modulate the expression of a nucleic acid encoding a IL-13 protein whose expression is dependent upon IL-9. Such assays may utilize any available means of monitoring for changes in the expression level of the nucleic acids encoding IL-13, IL-9 and/or IL-9 receptor proteins. As used herein, an agent is said to modulate the expression of a nucleic acid encoding a IL-13 protein, if it is capable of up- or down-regulating expression of the nucleic acid in a cell.

In one assay format, cell lines that contain reporter gene fusions between any region of the open reading frame of the IL-13 gene or fragments thereof under control of the gene's promoter and any assayable fusion partner. Numerous assayable fusion partners are known and readily available including the firefly luciferase gene and the gene encoding chloramphenicol acetyltransferase (Alam et al. (1990) Anal. Biochem. 188, 245-254). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding a IL -13 protein.

Additional assay formats may be used to monitor the ability of the agent to modulate the expression of a nucleic acid encoding a IL-13 protein associated with IL-9 expression and activity. For instance, mRNA expression may be monitored directly by hybridization to the nucleic acids encoding the IL-13, IL-9 and IL-9 receptor gene. Cell lines are exposed to the agent to be tested under appropriate conditions and time and total RNA or mRNA is isolated by standard procedures such those disclosed in Sambrook et al. (1989) Molecular Cloning: A Laboratory Manual, Cold Spring Harbor Laboratory Press.

Probes to detect differences in RNA expression levels between cells exposed to the agent and control cells may be prepared from the nucleic acids encoding the IL-13, IL-9 or IL-9 receptor gene. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarily which should exist between two nucleic acid strands in order to form a hybrid. Stringency should be chosen to maximize the difference in stability between the probe:target hybrid and potential probe:non-target hybrids.

Probes may be designed from the nucleic acids encoding the IL-13, IL-9 and/or IL -9 receptor gene through methods known in the art. For instance, the G+C content of the probe and the probe length can affect probe binding to its target sequence. Methods to optimize probe specificity are commonly available in Sambrook et al. (1989) Molecular Cloning: A Laboratory Manual, Cold Spring Harbor Laboratory Press; or Ausubel et al. (1995) Current Protocols in Molecular Biology, Greene Publishing Company.

Hybridization conditions are modified using known methods, such as those described by Sambrook et al. (1989) Molecular Cloning: A Laboratory Manual, Cold Spring Harbor Laboratory Press; or Ausubel et al. (1995) Current Protocols in Molecular Biology, Greene Publishing Company as required for each probe. Hybridization of total cellular RNA or RNA enriched for polyadenylated RNA can be accomplished in any available format. For instance, total cellular RNA or RNA enriched for polyadenylated RNA can be affixed to a solid support and the solid support exposed to at least one probe comprising at least one, or part of one of the sequences encoding the IL-13, IL-9 and/or IL-9 receptor gene under conditions in which the probe will specifically hybridize.

Alternatively, nucleic acid fragments comprising at least one, or part of one of the sequences of the invention can be affixed to a solid support, such as a porous glass wafer. The glass wafer can then be exposed to total cellular RNA or polyadenylated RNA from a sample under conditions in which the affixed sequences will specifically hybridize. Such glass wafers and hybridization methods are widely available, for example, those disclosed in WO 95/11755. By examining for the ability of a given probe to specifically hybridize to an RNA sample from an untreated cell population and from a cell population exposed to the agent, agents which up or down regulate the expression of a nucleic acid (SEQ ID NO: 11 for human or SEQ ID NO: 13 for murine) encoding the IL-13 protein (SEQ ID NO: 12 for human or SEQ ID NO: 14 for murine) are identified.

Hybridization for qualitative and quantitative analysis of mRNA may also be carried out by using a RNase Protection Assay (i.e., RPA, see Ma et al. (1996) Methods 10, 273-238). Briefly, an expression vehicle comprising cDNA encoding the gene product and a phage specific DNA dependent RNA polymerase promoter (e.g. T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising eighty percent formamide, 40 mM Pipes (pH 6.4), 0.4 M NaCl and 1 mM EDTA. The resulting hybrids are then digested in a buffer comprising 40 mg/ml ribonuclease A and 2 mg/ml ribonuclease. After deactivation and extraction of extraneous proteins, the samples are loaded onto urea/polyacrylamide gels for analysis.

In another assay format, agents which effect the expression of the instant gene products, cells or cell lines would first be identified which express said gene products physiologically. Cells and cell lines so identified, such as cells derived from the lung, would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines would be transduced or transfected with an expression vehicle (e.g. a plasmid or viral vector) construct comprising an operable non-translated 5'-promoter upstream of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art (see Sambrook et al. (1989) Molecular Cloning: A Laboratory Manual, Cold Spring Harbor Laboratory Press).

Cells or cell lines transduced or transfected as outlined above would then be contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides from disrupted cells are fractionated such that a polypeptide fraction is pooled and contacted with an antibody to be further processed by immunological assay (e.g., ELISA, immunoprecipitation or Western blot). The pool of proteins isolated from the "agent contacted" sample will be compared with a control sample where only the excipient is contacted with the cells and an increase or decrease in the immunologically generated signal from the "agent contacted" sample compared to the control will be used to distinguish the effectiveness of the agent.

Methods to Identify Agents that Modulate IL-13 Activity

The present invention provides methods for identifying agents that modulate at least one activity of a IL-13 protein associated with IL-9 expression and activity. Such methods or assays may utilize any means of monitoring or detecting the desired activity.

In one format, the specific activity of a IL-13 protein, normalized to a standard unit, between a cell population that has been exposed to the agent to be tested compared to an un-exposed control cell population may be assayed. Cell lines or populations are exposed to the agent to be tested under appropriate conditions and time. Cellular lysates may be prepared from the exposed cell line or population and a control, unexposed cell line or population. The cellular lysates are then analyzed with the probe.

Other screening assays may include measuring IL-13 activity by determining IL-9 and/or IL-9 receptor expression and/or activity. This could be accomplished by screening agents in cells containing IL-13 and IL-9 and/or the IL-9 receptor, determining IL-9 expression and/or activity by an appropriate method, and then screening agents in cell line not expressing IL-13 as a negative control. Agents which could act through IL-9 activation of IL-13 would be those increasing IL-9 and IL-13 expression in a IL-13-positive cell line, but not in a IL-13-negative cell line. 15-lipoxygenase and its isozyme 5-lipoxygenase activity assays could also be used where cells are stimulated with screening agents followed by exposure of the cell lysate (or sub-lysate fraction) to a specific lipoxygenase substrate to monitor the activation of intrinsic lipoxygenase activity. The association of specific binding proteins with IL-13 (e.g., IL-13 receptor) could also be used as an indication of IL-9 dependent activation of IL-13.

In yet another embodiment, one could test agents to identify which agents bind to IL-9 or its receptor to increase IL-13 expression and/or activity. Methods of determining binding of an agent to a receptor are well known in the art. Typically, the assays include the steps of incubating a source of the IL-9 or its receptor with a labeled agent, known to bind to IL -9 or its receptor, in the presence or absence of a test agent and determining the amount of bound labeled agent. The source of IL-9 receptor may either be cells expressing IL-9 receptor or some form of isolated IL-9 receptor as described herein. Cells expressing IL-9 receptor can be either cells which naturally express the IL-9 receptor or cells which have been engineered to express IL-9 receptor. Methods of recombinantly engineering a cell to express a protein such as IL-9 receptor are well known to those in the art. The labeled agent can be IL-9 or any IL-9 analog labeled such that it can be measured quantitatively (e.g., fluorescein labeled, GFP labeled, radiolabeled or europium labeled). Test agents that bind to the IL-9 receptor cause a reduction in the amount of labeled agent bound to the receptor, thereby reducing the signal level compared to that from control samples (absence of test compound). Binding of an agent to the IL-9 receptor can be used as an indicator of agents capable of inhibiting IL-9-dependent IL-13 expression and/or activity.

Antibody probes can be prepared by immunizing suitable mammalian hosts utilizing appropriate immunization protocols using the IL-9 and/or IL-9 receptor protein or antigen-containing fragments thereof. To enhance immunogenicity, these proteins or fragments can be conjugated to suitable carriers. Methods for preparing immunogenic conjugates with carriers such as BSA, KLH or other carrier proteins are well known in the art. In some circumstances, direct conjugation using, for example, carbodiimide reagents may be effective; in other instances linking reagents such as those supplied by Pierce Chemical Co. may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, use of monoclonal preparations is preferred for antibody probes. Immortalized cell lines which secrete the desired monoclonal antibodies may be prepared using standard methods, see e.g., Kohler & Milstein (1992) Biotechnology 24, 524-526 or modifications which effect immortalization of lymphocytes or spleen cells, as is generally known. The immortalized cell lines secreting the desired antibodies can be screened by immunoassay in which the antigen is the peptide hapten, polypeptide or protein. When the appropriate immortalized cell culture secreting the desired antibody is identified, the cells can be cultured either in vitro or by production in ascites fluid.

The desired monoclonal antibodies may be recovered from the culture supernatant or from the ascites supernatant. The intact antibodies or fragments thereof which contain the immunologically significant portion can be used as e.g., antagonists of binding between IL-9 (ligand) and its receptor, or alternatively as a IL-9 receptor agonists. Use of immunologically reactive fragments, such as Fab or Fab' fragments, is often preferable, especially for antibody probes, as these fragments are generally less immunogenic than the whole immunoglobulin. The antibodies or fragments may also be produced, using current technology, by recombinant means. Antibody regions that bind specifically to the desired regions of the protein can also be produced in the context of chimeras with multiple species origin.

Antibody regions that bind specifically to the desired regions of the IL-9 receptor can also be produced in the context of chimeras with multiple species origin, for instance, humanized antibodies. The antibody probes can therefore be a humanized antibody or a human antibody, as described in U.S. Pat. No. 5,585,089 or Riechmann et al. (1988) Nature 332, 323-327.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site or its conformation in connection with the agent's action. Agents can be rationally selected or rationally designed by utilizing the peptide sequences that make up these sites. The agents of the present invention can be, as examples, peptides, peptide mimetics, antibodies, antibody fragments, small molecules, vitamin derivatives, as well as carbohydrates. Peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies or fragments thereof that bind to IL-9 or the IL-9 receptor protein. Antibody agents can be obtained by immunization of suitable mammalian subjects with peptides, containing as antigenic regions, those portions of the protein intended to be targeted by the antibodies.

In yet another class of agents, the present invention includes peptide mimetics which mimic the three-dimensional structure of IL-9 and bind to the IL-9 receptor. Such peptide mimetics may have significant advantages over naturally-occurring peptides, including, for example: more economical production, greater chemical stability, enhanced pharmacological properties (half-life, absorption, potency, efficacy, etc.), altered specificity (e.g. a broad -spectrum of biological activities), reduced antigenicity and others.

In one form, mimetics are peptide-containing molecules that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

In another form, peptide analogs are commonly used in the pharmaceutical industry as non-peptide drugs with properties analogous to those of the template peptide. These types of non-peptide compounds are also referred to as peptide mimetics or peptidomimetics (Fauchere (1986) Adv. Drug Res. 15, 29-69; Veber & Freidinger (1985) Trends Neurosci. 8, 392-396; Evans et al. (1987) J. Med. Chem. 30, 1229-1239 which are incorporated herein by reference) and are usually developed with the aid of computerized molecular modeling.

Peptide mimetics that are structurally similar to therapeutically useful peptides may be used to produce an equivalent therapeutic or prophylactic effect. Generally, peptide mimetics are structurally similar to a paradigm polypeptide (i.e., a polypeptide that has a biochemical property or pharmacological activity), such as the binding domain of IL-9, but have one or more peptide linkages optionally replaced by a linkage by methods known in the art.

Labeling of peptide mimetics usually involves covalent attachment of one or more labels, directly or through a spacer (e.g. an amide group), to non-interfering position(s) on the peptide mimetic that are predicted by quantitative structure-activity data and molecular modeling. Such non-interfering positions generally are positions that do not form direct contacts with the macromolecule(s) to which the peptide mimetic binds to produce the therapeutic effect. Derivitization (e.g., labeling) of peptide mimetics should not substantially interfere with the desired biological or pharmacological activity of the peptide mimetic.

The use of peptide mimetics can be enhanced through the use of combinatorial chemistry to create drug libraries. The design of peptide mimetics can be aided by identifying amino acid mutations that increase or decrease binding of IL-9 to its receptor. Approaches that can be used include the yeast two hybrid method (see Chien et al. (1991) Proc. Natl. Acad. Sci. USA 88, 9578-9582) and using the phage display method. The two hybrid method detects protein -protein interactions in yeast (Fields et al. (1989) Nature 340, 245-246). The phage display method detects the interaction between an immobilized protein and a protein that is expressed on the surface of phages such as lambda and M13 (Amberg et al. (1993) Strategies 6, 2-4; Hogrefe et al. (1993) Gene 128, 119-126). These methods allow positive and negative selection for protein-protein interactions and the identification of the sequences that determine these interactions.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLE 1

IL-13 is Induced In Vivo by IL-9

Tg5 is a FVB mouse overexpressing the IL-9 gene as previously described (Renauld et al., (1994) Oncogene 9, 1327-1332). To confirm that IL-13 is induced by IL-9 in the lung, RNA from the lungs of Tg5 and FVB mice was isolated using Trizol as described by the manufacturer (Gibco/BRL). For Northern blot analysis, total RNA derived from Tg5 or FVB lungs was electrophoresed on 1.5% formaldehyde gels, transferred to nylon membranes and probed with a DNA fragment comprising the entire open reading frame of murine IL-13 cDNA. GAPDH was used as an internal control to assess for RNA loading.

The results of the expression studies demonstrated that IL-13 is specifically expressed in the lung of the IL-9 transgenic mouse but not in the parental strain (FIG. 1). This data demonstrated an effect of IL-9 on IL-13 expression in the lung, where IL-9 responsive cells contained within the lung express IL-13.

EXAMPLE 2

IL-13 is Induced In Vitro by IL-2

The murine bone marrow-derived mast cell line L138 and the thymic T-cell lymphoma BW51.47 were cultured in medium containing saturating concentrations of the indicated cytokines as follows: two days in the presence of 100 U/ml rIL-4 or 200 U/ml recombinant IL-9 for BW51.47 cells, two days in the presence of 1 ng/ml of rIL-3 or 200 U/ml rIL-9 for L138 cells.

Two independent strains of homozygous transgenic mice, designated Tg5 and Tg54, were used in this study. Both strains have circulating IL-9 levels>1 µg/ml, while IL-9 is undetectable in the serum of control FVB mice (Renauld et al. (1994) Oncogene 9, 1327-1332). Total RNA was extracted from the glandular stomach and lungs of six to eight week old Tg5, Tg54, or normal FVB mice (three mice per group).

Total cellular RNA was isolated from the cytokine treated cell lines or the mouse tissue by the guanidine thiocyanate/CsCl ultra-centrifugation method, and reverse transcription was performed on 10 µg total RNA with an oligo(dT) primer. cDNA corresponding to 100 ng of total RNA was amplified by PCR with the following IL-13 specific primers:

```
                                      (SEQ ID NO: 1)
sense          5' TGGGTGACTGCAGTCCTGGCT-3', (SEQ ID NO: 2)
antisense      5' GTTGCTTTGTGTAGCTGAGCA-3'.
```

An aliquot of the PCR reaction was run in a 1% agarose gel stained with ethidium bromide.

Figure 2:
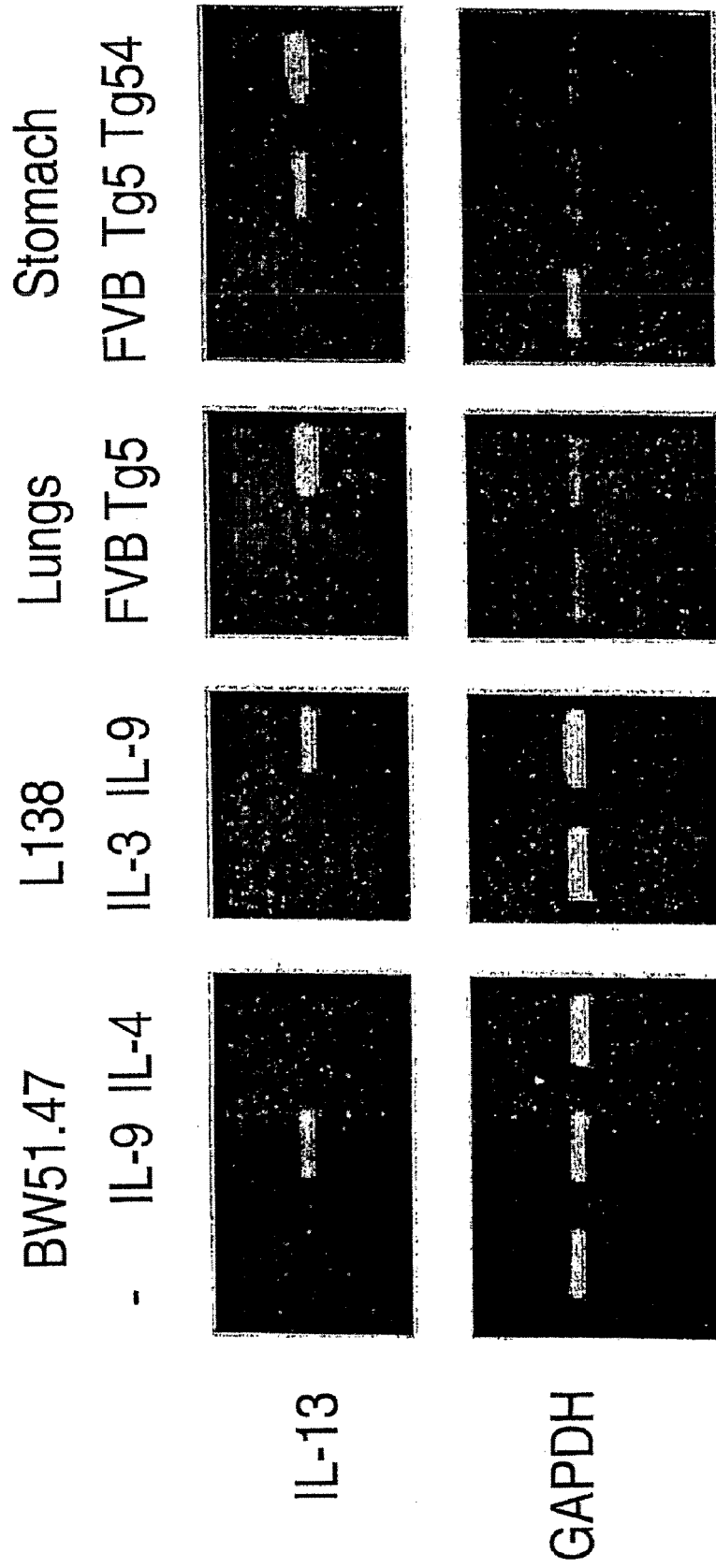
FIG. 2 depicts induction of IL-13 gene expression in IL-9 responsive cell lines and tissues of IL-9 transgenic mice.

As seen in FIG. 2, IL-13 message was seen only in the cell lines treated with IL-9 and not when treated with IL-3 or IL-4. In addition, the IL-13 message was only seen in the tissue of the IL-9 transgenic mice and not in the control mice which have no detectable levels of circulating IL-9. These data clearly indicate that IL-13 is up-regulated by IL-9 and suggest that IL-9 driven up-regulation can be blocked by IL-9 antagonists.

EXAMPLE 3

Inhibition of Antigen Induced Induction of IL-13 in the Lung with Anti-IL-9

IL-9 is a major mediator of the asthmatic response in man and mouse models of asthma (Nicolaides et al. (1997) Proc. Natl. Acad. Sci. 94, 13175-13180; McLane et al. (1998) Am. J. Respir. Cell Mol. Biol. 19, 713-720; Temann et al. (1998) J. Exp. Med. 188, 1307-1320; Levitt et al. (1999) Emerg. Thera. Targets 3, 1-11). The use of IL-9 blocking antibodies in antigen exposed mice suppresses the asthmatic-like phenotype (bronchial hyperresponsiveness, mucus overproduction and influx of inflammatory cells such as eosinophils).

Figure 3:
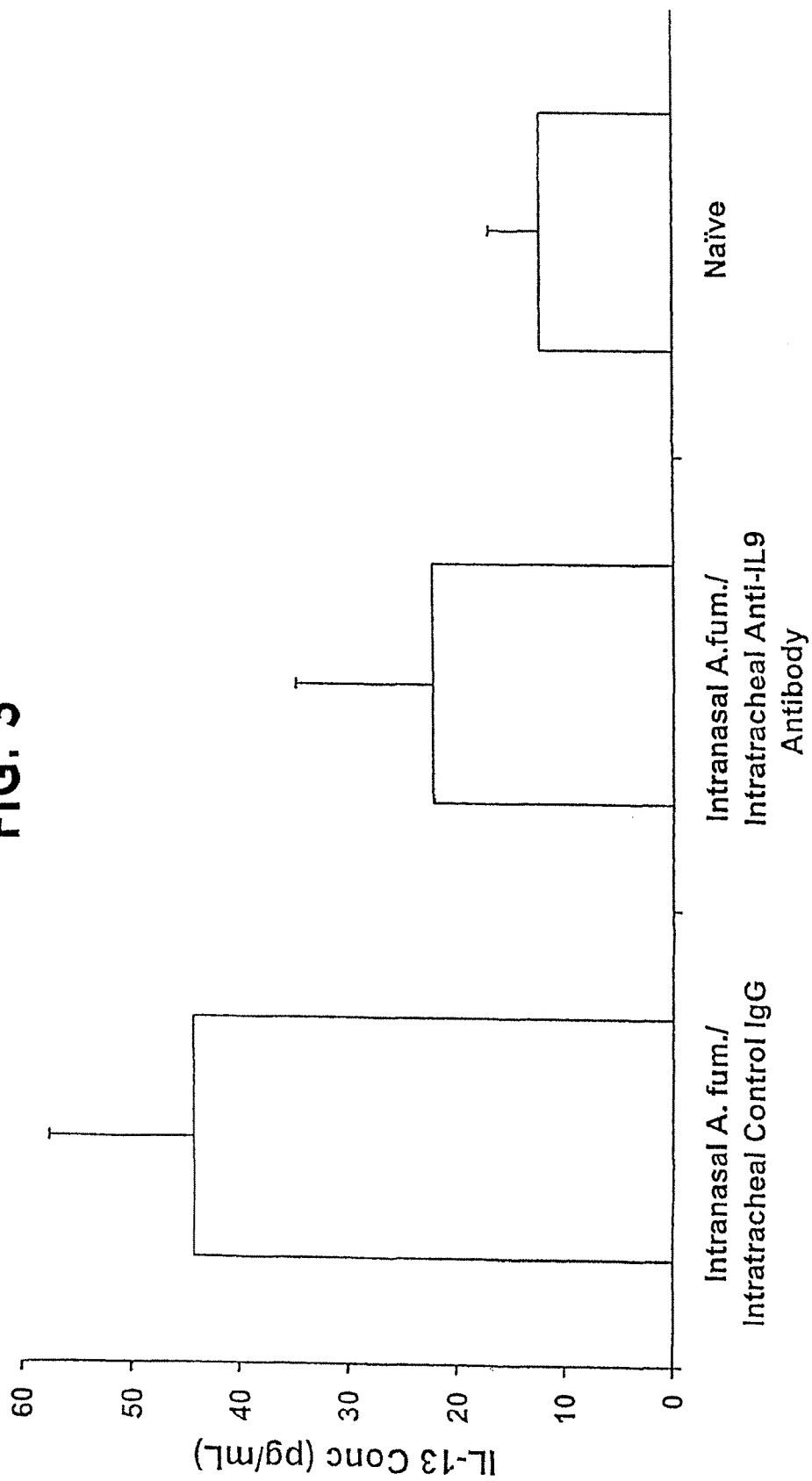
FIG. 3 depicts inhibition of IL-13 up-regulation with neutralizing IL-9 antibody in a murine model of asthma.

(B6D2)F1 mice were exposed to *Aspergillus fumagatus* antigen intranasally as described (McLane et al. (1998) Am. J. Respir. Cell Mol. Biol. 19, 713-720) on days zero, seven, fourteen, twenty-one and twenty-two. A subset of mice were also treated with 200 µg of anti-mIL-9 (Pharmingen hamster anti-mouse IL-9) or control IgG, by intratracheal instillation on days zero, seven, fourteen and twenty-one. All mice and IgG controls were tested for levels of IL-13 in bronchial lavage fluid using a standard ELISA (R&D Systems). As shown in FIG. 3, anti-IL-9 treatment was able to significantly suppress IL-13 to levels near that of naive. These data show that blocking the function of IL-9 can reduce the elevated levels of IL-13 resulting from exposure to antigen in a murine model of asthma.

EXAMPLE 4

Effect of Intra-Tracheal Instillation of IL-9 Antibody on IL-13 Gene Expression

Sixteen, male B6D2F1/J mice (Jackson Laboratories) aged four to five weeks were divided into four treatment groups. Animals in groups one through three each received 50 µl of *Aspergillus fumigatus* (Holister-Steir) allergenic extract (1:50 w/v in 10% glycerol) intranasally on days zero, seven, fourteen, twenty-one and twenty-two. Mice in group four received no treatment as a naive control. For antibody treatments, mice in group two received 200 μg of a control antibody (MAMA4, a non-neutralizing anti-murine IL-9 antibody, Genentech), whereas group three received 200 μg of D93 (hamster anti-murine IL-9 antibody with neutralizing activity, Pharmingen). Antibodies were administered intratracheally on days zero, seven, fourteen and twenty-one, approximately three hours prior to *A. fumigatus* exposure. On day twenty-three, approximately sixteen hours after the last *A. fumigatus* challenge, mice were anesthetized for measurement of airway hyperresponsiveness to intravenous serotonin. Mice in group one, as an infective control, received no antibody but received all challenge doses. Mice were terminally bled for serum immunoglobulin analysis, and bronchoalveolar lavage fluid was collected for cell counts and differentials. Finally, lungs were removed and flash frozen in liquid nitrogen.

Figure 4:
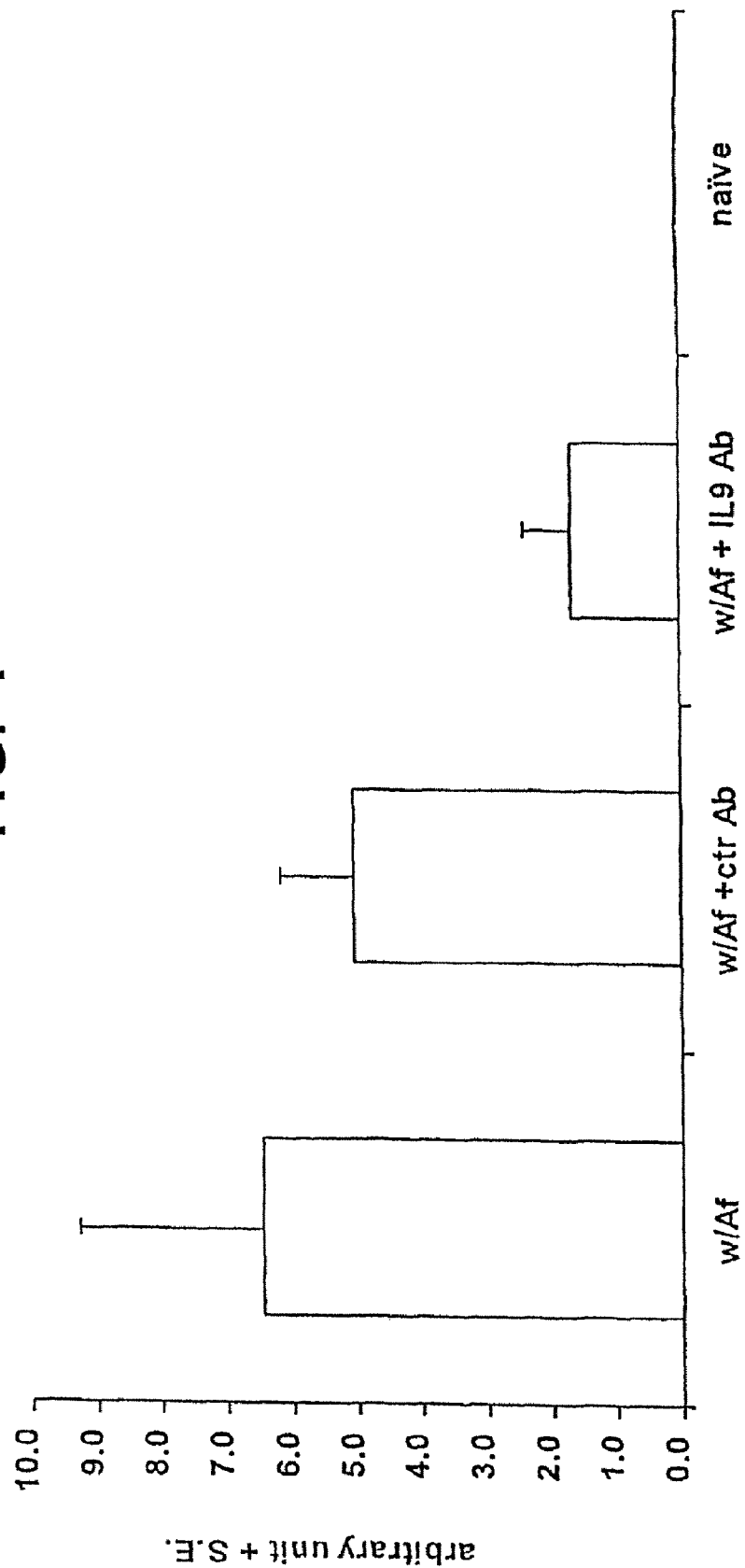
FIG. 4 depicts inhibition of IL-13 up-regulation with a neutralizing IL-9 antibody versus a non-neutralizing IL-9 control antibody, and non-antibody-treated infective control animals in a murine model of asthma.

RNA was isolated from frozen lungs using Trizol™ (Invitrogen) according to manufacturer's instructions. Contaminating genomic DNA was removed using the DNA-free kit (Ambion). IL-13 RNA was reverse-transcribed into cDNA using Omniscript™ (Qiagen). cDNA from approximately 125 ng starting RNA was used in each PCR reaction. Real-time PCR reaction was carried out in a 25 μL volume containing 1× Quantitect™ probe master mix (Qiagen), 0.4 μM each of the forward and reverse primers, 0.25 μM of Taqman™ probe, in an ABI PRISM 7700 Sequence Detection System (Applied Biosystems). Primers and probes were designed using Primer Express software. Amplification signals were generated through the cleavage of the 5' FAM reporter on the Taqman™ probe by the Taq polymerase. Upon cleavage of the probe, the 5' reporter was removed from the 3' quencher, resulting in fluorescent signals. The cycle number at which the fluorescent signal crosses an arbitrarily determined threshold is designated $C_T$. When the threshold is set in the exponential amplification phase, $C_T$ correlates inversely with the log of the starting copy number. To construct a standard curve, RNA from Concavalin A-stimulated murine splenocytes was reverse-transcribed, serially diluted to yield materials for standards. FIG. 4 shows that IL-13 expression is reduced in mice treated with the control anti-IL-9 antibody (w/Af+ctr Ab) versus infective controls (w/Af). However, mice treated with neutralizing anti-IL-9 antibody (w/Af+IL-9 Ab) demonstrated a significant decrease in IL-13 expression versus both the infective controls and the control antibody treated mice. One arbitrary unit (A.U.) is equivalent to 1 ng starting RNA from splenocytes. IL-13 and GAPDH mRNA levels for all samples were assayed in duplicates. IL-13 levels were normalized against GAPDH levels for each sample before calculation of the means and standard errors of the means.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

We claim:

1. A method of identifying an agent which modulates IL-13 expression and/or 15-lipoxygenase activity comprising:
    (a) contacting an experimental sample comprising cells expressing an IL-9 receptor with the agent in the presence of an IL-9 receptor ligand and measuring IL-13 expression and/or 15-lipoxygenase activity in the experimental cell; and
    (b) contacting a control sample comprising cells that do not express an IL-9 receptor with the agent in the presence of an IL-9 receptor ligand and measuring IL-13 expression and/or 15-lipoxygenase activity in the control cells;
    wherein a decrease or increase in IL-13 expression and/or 15-lipoxygenase activity in the experimental cells compared to the control indicates that the agent is capable of modulating IL-13 expression and/or 15-lipoxygenase activity.

2. The method of claim 1 wherein said IL-9 receptor ligand is selected from the group consisting of IL-9 or a fragment thereof, an IL-9 analog and an IL-9 peptide mimetic.

3. The method of claim 1, wherein measuring expression of IL-13 comprises measuring expression of a nucleic acid encoding IL-13 or a fragment thereof.

4. The method of claim 3, wherein the IL-13 expression comprises measuring the changes in the nucleic acid encoding an amino acid sequence comprising the amino acid sequence of SEQ ID NO: 12 or a fragment thereof.

5. The method of claim 3, wherein the IL-13 expression comprises measuring the changes in the nucleic acid sequence of SEQ ID NO: 11 or a fragment thereof.

6. The method of claim 1, further comprising measuring the changes in the expression of one or more nucleic acid encoding IL-9 or a fragment thereof.

7. The method of claim 6, wherein the nucleic acid is mRNA.

8. The method of claim 1, further comprising measuring the changes in the expression of one or more nucleic acid encoding IL-9 receptor or a fragment thereof.

9. The method of claim 8, wherein the nucleic acid is mRNA.

10. The method of claim 1, wherein the expression of IL-13 is linked to a reporter gene in the experimental and control cells.

11. The method of claim 10, wherein the step of measuring IL-13 expression comprises measuring the expression of the reporter gene.

12. The method of claim 10, wherein the reporter gene is firefly luciferase or chloramphenicol acteyltransferase.

* * * * *